(12) United States Patent
Gerster et al.

(10) Patent No.: US 8,980,134 B2
(45) Date of Patent: Mar. 17, 2015

(54) STABILIZATION AND SURFACE MODIFICATION OF ORGANIC MATERIALS

(75) Inventors: Michèle Gerster, Binningen (CH); Manuel Mihalic, Grenzach-Wyhlen (DE)

(73) Assignee: BASF SE, Ludwigshafen (DE)

( * ) Notice: Subject to any disclaimer, the term of this patent is extended or adjusted under 35 U.S.C. 154(b) by 1186 days.

(21) Appl. No.: 12/937,731

(22) PCT Filed: Mar. 31, 2009

(86) PCT No.: PCT/EP2009/053770
§ 371 (c)(1),
(2), (4) Date: Jan. 14, 2011

(87) PCT Pub. No.: WO2009/127514
PCT Pub. Date: Oct. 22, 2009

(65) Prior Publication Data
US 2011/0160357 A1    Jun. 30, 2011

(30) Foreign Application Priority Data

Apr. 17, 2008 (EP) .................................... 08154680

(51) Int. Cl.
| | | |
|---|---|---|
| *C09K 15/12* | (2006.01) | |
| *C09K 15/28* | (2006.01) | |
| *C08K 5/46* | (2006.01) | |
| *C07D 327/06* | (2006.01) | |
| *C07C 321/20* | (2006.01) | |
| *C08L 23/12* | (2006.01) | |
| *C07B 63/04* | (2006.01) | |
| *C07C 323/16* | (2006.01) | |
| *C07C 323/52* | (2006.01) | |

(52) U.S. Cl.
CPC .............. *C07D 327/06* (2013.01); *C07B 63/04* (2013.01); *C07C 323/16* (2013.01); *C07C 323/52* (2013.01)
USPC ........... 252/406; 352/402; 352/403; 352/407; 524/83; 549/15; 568/51

(58) Field of Classification Search
USPC .................... 252/402, 403, 406, 407; 524/83; 549/15; 568/51
See application file for complete search history.

(56) References Cited

U.S. PATENT DOCUMENTS 3,641,054 A * 2/1972 Martin ............................ 549/14
4,621,109 A  11/1986 Lechtken
2010/0160411 A1 * 6/2010 Stack et al. .................... 514/434

FOREIGN PATENT DOCUMENTS

JP          01236252 A     9/1989

OTHER PUBLICATIONS

English language abstract of JP 01 236252 printed on Jan. 19, 2011.
Sanz-Asensio et al., Journal of Chromatography, vol. 840, No. 2, Apr. 30, 1999, pp. 235-247.
M.G. Burdon et al., J. Am. Chem. Soc. vol. 88, No. 24, 1966, pp. 5855-5864.
Tomonori Katada, et al., J. Chem. Soc. Perkin Trans. I, 1984, pp. 2648-2653.
Abdou Sall et al., Journal of Chemical Research, Synopses, (7), p. 266, (1995).
Burka, et al., Reproductive Toxicology, vol. 7, (1), pp. 81-86, 1993.
Gerster et al., Synthesis, 2009, No. 22, pp. 3848-3852.
Wilson et al., Inorganica Chimica Acta, 192 (2), pp. 219-25, 1992.
Modica et al., Journal of Organic Chemistry, 66 (1) pp. 41-52 (2001).
H. Meier, Phosphorus, Sulfur, Silicon(1999) pp. 275-300.
Mayer et al., Chemical Abstracts Service, Database accession No. 17:21832, (1923).

* cited by examiner

*Primary Examiner* — Joseph D Anthony
(74) *Attorney, Agent, or Firm* — Oblon, McClelland, Maier & Neustadt, L.L.P.

(57) ABSTRACT

Organic materials which possess outstanding stability to oxidative, thermal or light-induced degradation and/or are able to reduce the surface energy of organic materials comprise at least one compound of the formula (I) wherein the general symbols are as defined in claim 1.

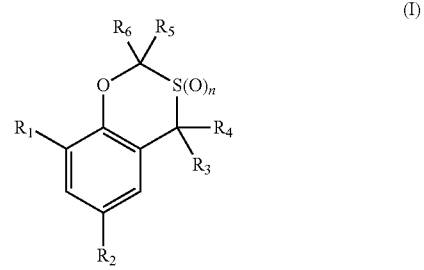

13 Claims, No Drawings

STABILIZATION AND SURFACE MODIFICATION OF ORGANIC MATERIALS

The present invention relates to compositions comprising an organic material, preferably a polymer or a lubricant, and to benzoxathiane derivatives, as well as to the use thereof for stabilizing organic materials against oxidative, thermal or light-induced degradation and/or as reducers of surface energy for organic materials.

The known stabilizers do not satisfy in every respect the high requirements which a stabilizer is required to meet, especially with regard to shelf life, water absorption, sensitivity to hydrolysis, in-process stabilization, color properties, volatility, migration behavior, compatibility and improvement in protection against light. As a result there continues to be a need for effective stabilizers for organic materials that are sensitive to oxidative, thermal and/or light-induced degradation and/or meet the requirements as reducers of surface energy for organic materials, for example, for increasing the oil and water repellency of organic materials.

It has now been found that benzoxathiane derivatives are particularly suitable for use as stabilizers for organic materials that are susceptible to oxidative, thermal or light-induced degradation and/or as reducers of surface energy for organic materials.

Accordingly, the invention relates to a composition comprising
 a) an organic material subject to oxidative, thermal or light-induced degradation, and
 b) at least one compound of the formula I

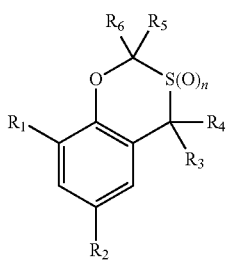
(I)

wherein $R_1$ and $R_2$ independently of each other are hydrogen, $C_1$-$C_{25}$alkyl, $C_2$-$C_{25}$alkenyl, unsubstituted or with $C_1$-$C_4$alkyl substituted phenyl; unsubstituted or with $C_1$-$C_4$alkyl substituted $C_7$-$C_9$phenylalkyl; —CH($R_7$)—S(O)$_n$—$R_8$ or —CH($R_7$)—S(O)$_n$—CH$_2$—CH($R_7$)—$R_9$, $R_3$ and $R_4$ independently of each other are hydrogen, $C_1$-$C_{25}$alkyl, unsubstituted or with $C_1$-$C_4$alkyl substituted phenyl, $R_5$ and $R_6$ independently of each other are hydrogen, $C_1$-$C_{25}$alkyl, $C_2$-$C_{25}$alkyl interrupted by oxygen; unsubstituted or with $C_1$-$C_4$alkyl substituted phenyl; halogen, —CN, —NO$_2$,

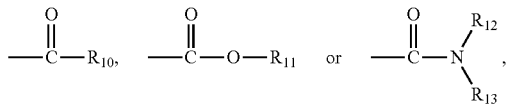

$R_7$ is hydrogen, $C_1$-$C_{12}$alkyl,

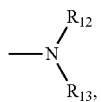

unsubstituted or with halogen or $C_1$-$C_4$alkyl substituted phenyl;

$R_8$ is a monovalent perfluorinated alkyl or alkenyl, linear or branched organic radical having four to twenty fully fluorinated carbon atoms, $R_9$ is —CN, —S(O)$_n$—$R_{10}$,

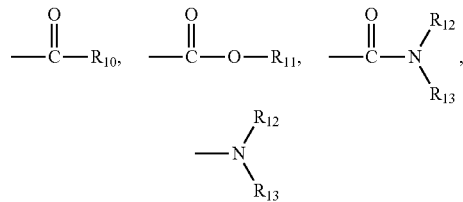

or —NO$_2$, $R_{10}$ is hydrogen, $C_1$-$C_{25}$alkyl, $C_7$-$C_9$phenylalkyl, unsubstituted or $C_1$-$C_4$alkyl-substituted phenyl; unsubstituted or $C_1$-$C_4$alkyl-substituted $C_5$-$C_8$cycloalkyl;

$R_{11}$ is hydrogen, alkali metal, $C_1$-$C_{25}$alkyl, $C_7$-$C_9$phenylalkyl, unsubstituted or $C_1$-$C_4$alkyl-substituted phenyl; unsubstituted or $C_1$-$C_4$alkyl-substituted $C_5$-$C_8$cycloalkyl; or $C_3$-$C_{25}$alkyl which is interrupted by oxygen or sulfur;

$R_{12}$ and $R_{13}$ independently of one another are hydrogen, $C_1$-$C_{25}$alkyl, $C_1$-$C_4$alkanoyl, $C_7$-$C_9$phenylalkyl, unsubstituted or $C_1$-$C_4$alkyl-substituted phenyl; or $R_{12}$ and $R_{13}$, together with the nitrogen atom to which they are attached, form a 5-, 6- or 7-membered heterocyclic ring which is unsubstituted or is substituted by $C_1$-$C_4$alkyl or is interrupted by oxygen, sulfur or

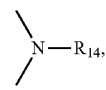

$R_{14}$ is hydrogen, $C_1$-$C_8$alkyl or benzyl, and
n is 0 1 or 2.

Alkyl having up to 25 carbon atoms is a branched or unbranched radical, for example methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl, eicosyl or docosyl.

Alkanoyl having up to 4 carbon atoms is a branched or unbranched radical, for example formyl, acetyl, propionyl, butanoyl or pivaloyl.

Alkenyl having 2 to 25 carbon atoms is a branched or unbranched radical such as, for example, vinyl, propenyl, 2-butenyl, 3-butenyl, isobutenyl, n-2,4-pentadienyl, 3-methyl-2-butenyl, n-2-octenyl, n-2-dodecenyl, iso-dodecenyl, oleyl, n-2-octadecenyl or n-4-octadecenyl.

$C_1$-$C_4$Alkyl-substituted phenyl, which preferably contains 1 to 3, especially 1 or 2 alkyl groups, is, for example, o-, m- or p-methylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2-methyl-6-ethylphenyl, 4-tert-butylphenyl, 2-ethylphenyl or 2,6-diethylphenyl.

$C_7$-$C_9$Phenylalkyl is, for example, benzyl, α-methylbenzyl, α,α-dimethylbenzyl or 2-phenylethyl.

With $C_1$-$C_4$alkyl substituted $C_7$-$C_9$phenylalkyl is, for example 4-methylbenzyl, 4-methyl-α-methylbenzyl, 4-methyl-α,α-dimethylbenzyl or 4-methylphenyl-2-ethyl.

$C_3$-$C_{25}$Alkyl interrupted by oxygen or sulfur is, for example, $CH_3$—O—$CH_2CH_2$—, $CH_3$—S—$CH_2CH_2$—, $CH_3$—O—$CH_2CH_2$—O—$CH_2CH_2$—, $CH_3$—(O—$CH_2CH_2$—)$_2$O—$CH_2CH_2$—, $CH_3$—(O—$CH_2CH_2$—)$_3$O—$CH_2CH_2$— or $CH_3$—(O—$CH_2CH_2$—)$_4$O—$CH_2CH_2$—.

Halogen is for example fluoro, chloro, bromo or iodo.

A monovalent perfluorinated alkyl or alkenyl, linear or branched organic radical having four to twenty fully fluorinated carbon atoms is for example —$(CF_2)_mCF_3$ or —$CH_2CH_2(CF_2)_mCF_3$ wherein m is 3 to 19, preferably 3 to 12. The prefluoroalkyl moieties represent also mixtures of perfluoroalkyl moieties which means that $R_8$ usually concomitantly contains a small fraction of perfluoroalkyl groups with a lower number of carbon atoms and small fraction of perfluoroalkyl groups with a higher number of carbon atoms.

Unsubstituted or $C_1$-$C_4$alkyl-substituted $C_5$-$C_8$cycloalkyl is, for example, cyclopentyl, methylcyclopentyl, dimethylcyclopentyl, cyclohexyl, methylcyclohexyl, dimethylcyclohexyl, trimethylcyclohexyl, tert-butylcyclohexyl, cycloheptyl or cyclooctyl. Preference is given to cyclohexyl and tert-butylcyclohexyl.

Where $R_{12}$ and $R_{13}$ together with the nitrogen atom to which they are attached, form a 5-, 6- or 7-membered heterocyclic ring which is unsubstituted or is substituted by $C_1$-$C_4$alkyl or is interrupted by oxygen, sulfur or

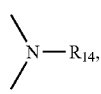

this denotes, for example, the following radicals:

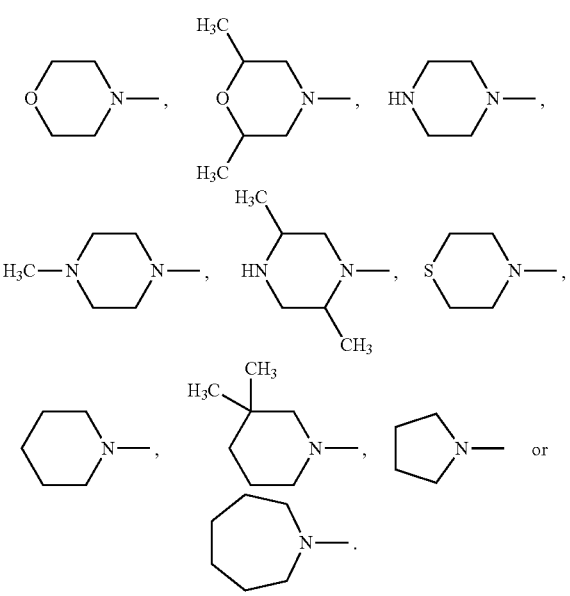

$R_{12}$ and $R_{13}$ preferably form with the nitrogen atom to which they are attached, a 6-membered heterocyclic ring interrupted by oxygen, such as, for example,

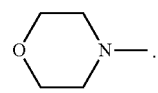

Compositions which are of interest include those comprising as component (b) a compound of the formula I, wherein $R_1$ and $R_2$ independently of each other are hydrogen, $C_1$-$C_{18}$alkyl, $C_2$-$C_{18}$alkenyl, unsubstituted or with $C_1$-$C_4$alkyl substituted phenyl; unsubstituted or with $C_1$-$C_4$alkyl substituted $C_7$-$C_9$-phenylalkyl; —CH($R_7$)—S(O)$_n$—$R_8$ or —CH($R_7$)—S(O)$_n$—$CH_2$—CH($R_7$)—$R_9$, $R_3$ and $R_4$ independently of each other are hydrogen, $C_1$-$C_{18}$alkyl, unsubstituted or with $C_1$-$C_4$alkyl substituted phenyl, $R_5$ and $R_6$ independently of each other are hydrogen, $C_1$-$C_{18}$alkyl, $C_2$-$C_{18}$alkyl interrupted by oxygen; unsubstituted or with $C_1$-$C_4$alkyl substituted phenyl; halogen, —CN,

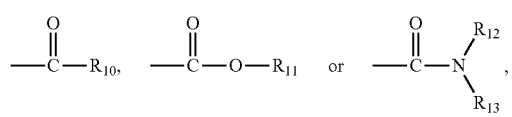

$R_7$ is hydrogen, $C_1$-$C_{12}$alkyl or phenyl, $R_8$ is a monovalent perfluorinated alkyl or alkenyl, linear or branched organic radical having four to twenty fully fluorinated carbon atoms, $R_9$ is —CN, —S(O)$_n$—$R_{10}$,

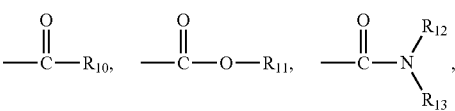

or —$NO_2$, $R_{10}$ is hydrogen, $C_1$-$C_{18}$alkyl, $C_7$-$C_9$phenylalkyl, unsubstituted or $C_1$-$C_4$alkyl-substituted phenyl; unsubstituted or $C_1$-$C_4$alkyl-substituted $C_5$-$C_8$cycloalkyl;

$R_{11}$ is hydrogen, $C_1$-$C_{18}$alkyl, $C_7$-$C_9$phenylalkyl, unsubstituted or $C_1$-$C_4$alkyl-substituted phenyl; unsubstituted or $C_1$-$C_4$alkyl-substituted $C_5$-$C_8$cycloalkyl; or $C_3$-$C_{18}$alkyl which is interrupted by oxygen or sulfur;

$R_{12}$ and $R_{13}$ independently of one another are hydrogen, $C_1$-$C_{18}$alkyl, $C_7$-$C_9$phenylalkyl, unsubstituted or $C_1$-$C_4$alkyl-substituted phenyl; or $R_{12}$ and $R_{13}$, together with the nitrogen atom to which they are attached, form a 5-, 6- or 7-membered heterocyclic ring which is unsubstituted or is substituted by $C_1$-$C_4$alkyl or is interrupted by oxygen, sulfur or

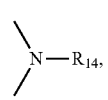

$R_{14}$ is hydrogen, $C_1$-$C_8$alkyl or benzyl, and n is 0 1 or 2.

Compositions that are of interest include those comprising as component (b) at least one compound of the formula I wherein $R_3$ and $R_5$ are hydrogen.

Preference is given to compositions comprising as component (b) at least one compound of the formula I wherein $R_1$ and $R_2$ independently of each other are $C_1$-$C_4$alkyl, —CH($R_7$)—S(O)$_n$—$R_8$ or —CH($R_7$)—S(O)$_n$—CH$_2$—CH($R_7$)—$R_9$, $R_7$ is hydrogen or $C_1$-$C_4$alkyl, $R_8$ is a monovalent perfluorinated alkyl or alkenyl, linear or branched organic radical having four to twenty fully fluorinated carbon atoms, $R_9$ is

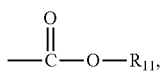

$R_{11}$ is hydrogen or $C_1$-$C_{12}$alkyl, and n is 0, 1 or 2.

Preference is given to compositions comprising as component (b) at least one compound of the formula I wherein $R_1$ and $R_2$ independently of each other are $C_1$-$C_4$alkyl, —CH($R_7$)—S(O)$_n$—$R_8$ or —CH($R_{7a}$)—S(O)$_n$—CH$_2$—CH($R_{7b}$)—$R_9$, $R_7$, $R_{7a}$ and $R_{7b}$ independently of each other are hydrogen or $C_1$-$C_4$alkyl, $R_8$ is a monovalent perfluorinated alkyl or alkenyl, linear or branched organic radical having four to twenty fully fluorinated carbon atoms, $R_9$ is

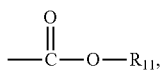

$R_{11}$ is hydrogen or $C_1$-$C_{12}$alkyl, and n is 0, 1 or 2.

Preference is also given to compositions comprising as component (b) at least one compound of the formula I wherein $R_8$ is —(CF$_2$)$_m$CF$_3$ or —CH$_2$—CH$_2$—(CF$_2$)$_m$CF$_3$, and m is 3 to 12.

Preference is likewise given to compositions comprising as component (b) at least one compound of the formula I wherein $R_1$ and $R_2$ independently of each other are hydrogen, $C_1$-$C_{12}$alkyl, phenyl, benzyl, —CH($R_7$)—S(O)$_n$—$R_8$ or —CH($R_7$)—S(O)$_n$—CH$_2$—CH($R_7$)—$R_9$, $R_3$ and $R_4$ independently of each other are hydrogen, $C_1$-$C_{12}$alkyl or phenyl, $R_5$ and $R_6$ independently of each other are hydrogen, $C_1$-$C_{12}$alkyl, phenyl, halogen, —CN,

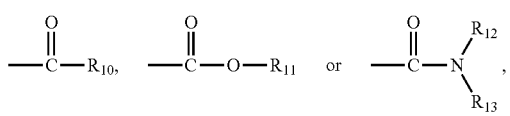

$R_7$ is hydrogen or $C_1$-$C_{12}$alkyl, $R_8$ is —(CF$_2$)$_m$CF$_3$ or —CH$_2$—CH$_2$—(CF$_2$)$_m$CF$_3$, $R_9$ is —CN,

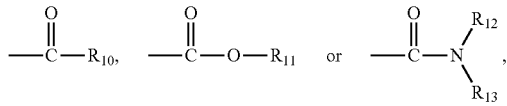

$R_{10}$ is $C_1$-$C_{12}$alkyl, $C_7$-$C_9$phenylalkyl, phenyl or $C_5$-$C_8$cycloalkyl, $R_{11}$ is hydrogen, $C_1$-$C_{12}$alkyl, benzyl, phenyl or $C_5$-$C_8$cycloalkyl or $C_3$-$C_{18}$alkyl, $R_{12}$ and $R_{13}$ independently of one another are hydrogen, $C_1$-$C_{12}$alkyl, benzyl, phenyl; or $R_{12}$ and $R_{13}$, together with the nitrogen atom to which they are attached, form a 6-membered heterocyclic ring, m is 3 to 12, and n is 0 1 or 2.

Particular preference is given to compositions comprising as component (b) at least one compound of the formula I wherein $R_1$ is $C_1$-$C_4$alkyl, —CH($R_7$)—S(O)$_n$—$R_8$ or —CH($R_7$)—S(O)$_n$—CH$_2$—CH($R_7$)—$R_9$, $R_2$ is $C_1$-$C_4$alkyl, —CH($R_7$)—S(O)$_n$—$R_8$ or —CH($R_7$)—S(O)$_n$—CH$_2$—CH($R_7$)—$R_9$, $R_3$ is hydrogen, $R_4$ is hydrogen or phenyl, $R_5$ is hydrogen, $R_6$ is hydrogen or phenyl, $R_7$ is hydrogen, $R_8$ is —CH$_2$—CH$_2$—(CF$_2$)$_3$CF$_3$ or —CH$_2$—CH$_2$—(CF$_2$)$_7$CF$_3$, $R_9$ is

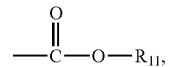

$R_{11}$ is hydrogen or $C_1$-$C_8$alkyl, and n is 0 1 or 2.

Preference is also given to compositions comprising as component (b) at least one compound of the formula I wherein Preference is also given to compositions comprising as component (b) at least one compound of the formula I wherein $R_9$ is —CN, —S(O)$_n$—$R_{10}$,

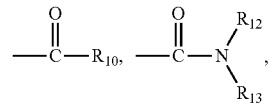

or —NO$_2$.

Preference is also given to compositions comprising as component (b) at least one compound of the formula I wherein $R_{11}$ is $C_1$-$C_{25}$alkyl, $C_7$-$C_9$phenylalkyl, unsubstituted or $C_1$-$C_4$alkyl-substituted phenyl; unsubstituted or $C_1$-$C_4$alkyl-substituted $C_5$-$C_8$cycloalkyl; or $C_3$-$C_{25}$alkyl which is interrupted by oxygen or sulfur.

Preference is also given to compositions comprising as component (b) at least one compound of the formula I wherein $R_{12}$ and $R_{13}$ independently of one another are $C_1$-$C_{25}$alkyl, $C_1$-$C_4$alkanoyl, $C_7$-$C_9$phenylalkyl, unsubstituted or $C_1$-$C_4$alkyl-substituted phenyl; or $R_{12}$ and $R_{13}$, together with the nitrogen atom to which they are attached, form a 5-, 6- or 7-membered heterocyclic ring which is unsubstituted or is substituted by $C_1$-$C_4$alkyl or is interrupted by oxygen, sulfur or

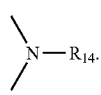
Especially preferred are compounds 101-120 according to Table 1 and the following compounds 121-140.
(121)
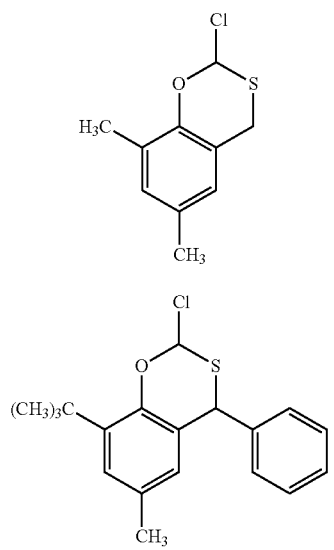
(122)
(123)
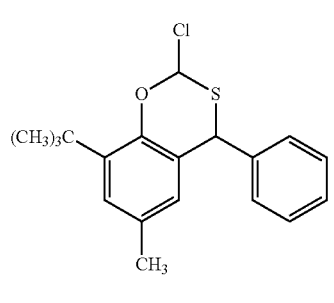
(124)
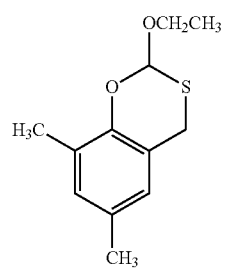
(125)
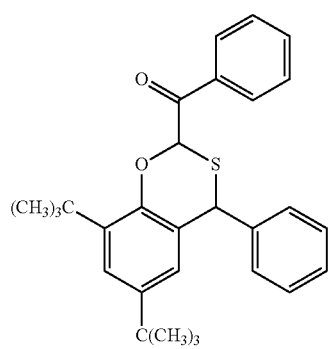
(126)
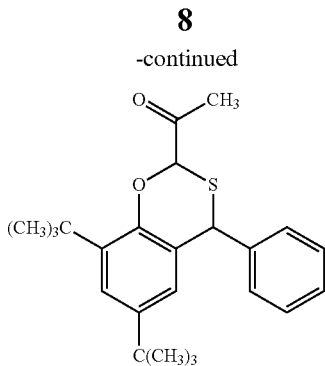
(127)
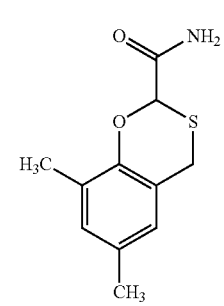
(128)
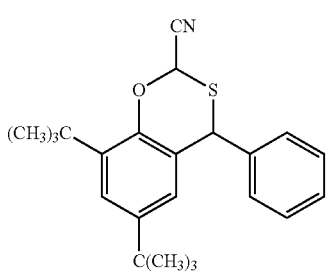
(129)
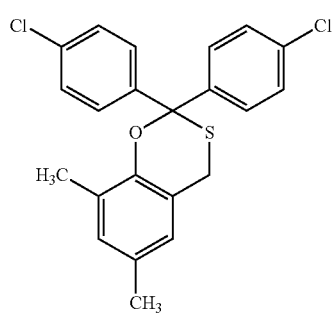
(130)
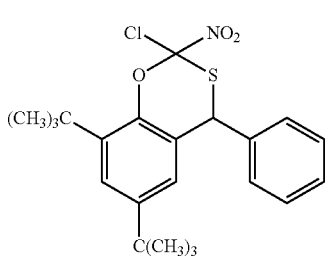

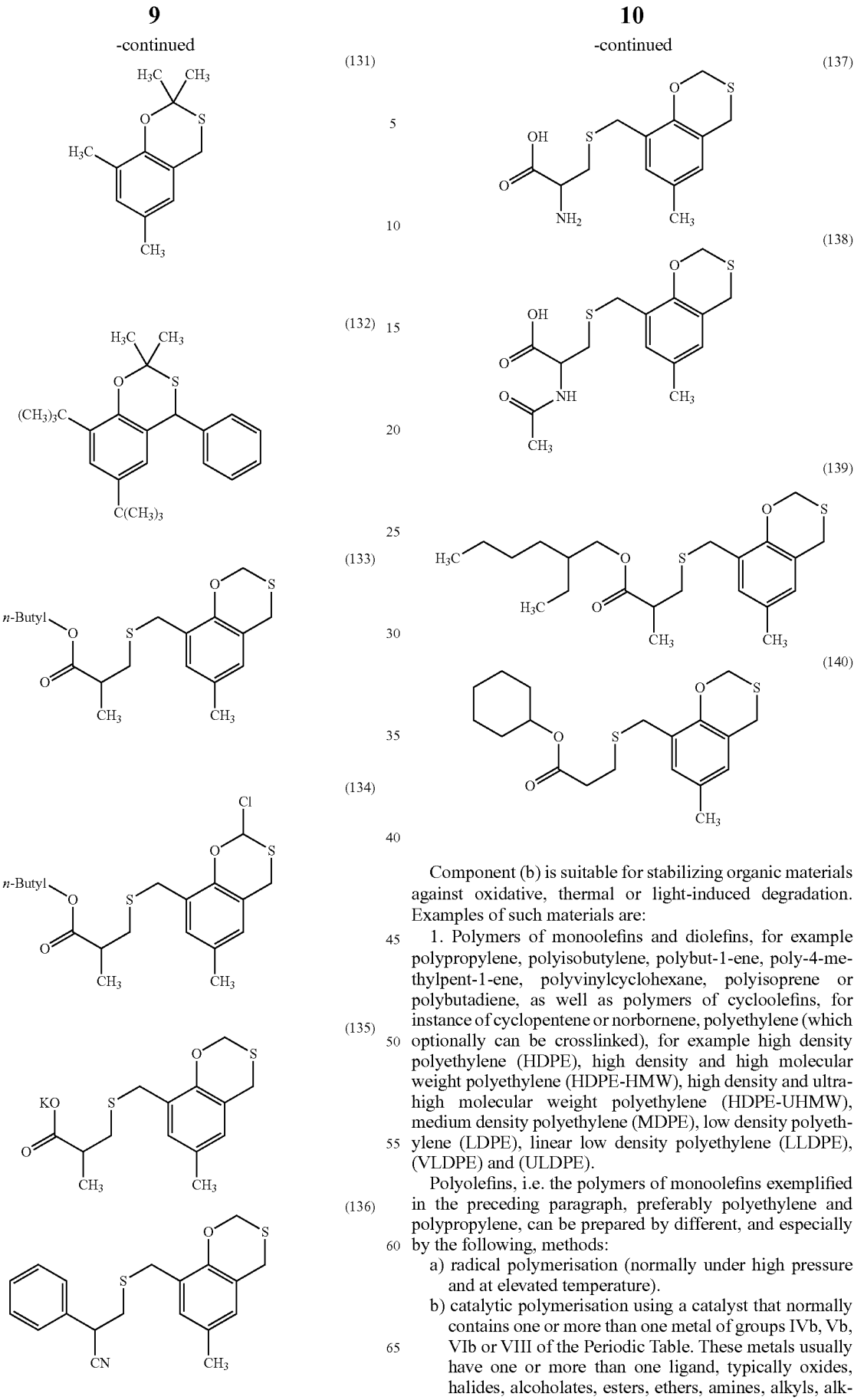

Component (b) is suitable for stabilizing organic materials against oxidative, thermal or light-induced degradation. Examples of such materials are:

1. Polymers of monoolefins and diolefins, for example polypropylene, polyisobutylene, polybut-1-ene, poly-4-methylpent-1-ene, polyvinylcyclohexane, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultra-high molecular weight polyethylene (HDPE-UHMW), medium density polyethylene (MDPE), low density polyethylene (LDPE), linear low density polyethylene (LLDPE), (VLDPE) and (ULDPE).

Polyolefins, i.e. the polymers of monoolefins exemplified in the preceding paragraph, preferably polyethylene and polypropylene, can be prepared by different, and especially by the following, methods:
  a) radical polymerisation (normally under high pressure and at elevated temperature).
  b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, ethylene/vinylcyclohexane copolymers, ethylene/cycloolefin copolymers (e.g. ethylene/norbornene like COC), ethylene/1-olefins copolymers, where the 1-olefin is generated in-situ; propylene/butadiene copolymers, isobutylene/isoprene copolymers, ethylene/vinylcyclohexene copolymers, ethylene/alkyl acrylate copolymers, ethylene/alkyl methacrylate copolymers, ethylene/vinyl acetate copolymers or ethylene/acrylic acid copolymers and their salts (ionomers) as well as terpolymers of ethylene with propylene and a diene such as hexadiene, dicyclopentadiene or ethylidenenorbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$-$C_9$) including hydrogenated modifications thereof (e.g. tackifiers) and mixtures of polyalkylenes and starch.

Homopolymers and copolymers from 1.)-4.) may have any stereostructure including syndiotactic, isotactic, hemi-isotactic or atactic; where atactic polymers are preferred. Stereoblock polymers are also included.

5. Polystyrene, poly(p-methylstyrene), poly(α-methylstyrene).

6. Aromatic homopolymers and copolymers derived from vinyl aromatic monomers including styrene, α-methylstyrene, all isomers of vinyl toluene, especially p-vinyltoluene, all isomers of ethyl styrene, propyl styrene, vinyl biphenyl, vinyl naphthalene, and vinyl anthracene, and mixtures thereof. Homopolymers and copolymers may have any stereostructure including syndiotactic, isotactic, hemi-isotactic or atactic; where atactic polymers are preferred. Stereoblock polymers are also included.

6a. Copolymers including aforementioned vinyl aromatic monomers and comonomers selected from ethylene, propylene, dienes, nitriles, acids, maleic anhydrides, maleimides, vinyl acetate and vinyl chloride or acrylic derivatives and mixtures thereof, for example styrene/butadiene, styrene/acrylonitrile, styrene/ethylene (interpolymers), styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

6b. Hydrogenated aromatic polymers derived from hydrogenation of polymers mentioned under 6.), especially including polycyclohexylethylene (PCHE) prepared by hydrogenating atactic polystyrene, often referred to as polyvinylcyclohexane (PVCH).

6c. Hydrogenated aromatic polymers derived from hydrogenation of polymers mentioned under 6a.).

Homopolymers and copolymers may have any stereostructure including syndiotactic, isotactic, hemi-isotactic or atactic; where atactic polymers are preferred. Stereoblock polymers are also included.

7. Graft copolymers of vinyl aromatic monomers such as styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated and brominated copolymer of isobutylene-isoprene (halobutyl rubber), chlorinated or sulfo-chlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from α,β-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides, polyetherimides, polyesterimides, polyhydantoins and polybenzimidazoles.

18. Polyesters derived from dicarboxylic acids and diols and/or from hydroxycarboxylic acids or the corresponding lactones or lactides, for example polyethylene terephthalate, polybutylene terephthalate, poly-1,4-dimethylolcyclohexane terephthalate, polyalkylene naphthalate and polyhydroxybenzoates as well as copolyether esters derived from hydroxyl-terminated polyethers, and also polyesters modified with polycarbonates or MBS. Copolyesters may comprise, for example—but are not limited to—polybutylenesuccinate/terephtalate, polybutyleneadipate/terephthalate, polytetramethyleneadipate/terephthalate, polybutylensuccinate/adipate, polybutylensuccinate/carbonate, poly-3-hydroxybutyrate/octanoate copolymer, poly-3-hydroxybutyrate/hexanoate/decanoate terpolymer. Furthermore, aliphatic polyesters may comprise, for example—but are not limited to—the class of poly(hydroxyalkanoates), in particular, poly(propiolactone), poly(butyrolactone), poly(pivalolactone), poly(valerolactone) and poly(caprolactone), polyethylenesuccinate, polypropylenesuccinate, polybutylenesuccinate, polyhexamethylenesuccinate, polyethyleneadipate, polypropyleneadipate, polybutyleneadipate, polyhexamethyleneadipate, polyethyleneoxalate, polypropyleneoxalate, polybutyleneoxalate, polyhexamethyleneoxalate, polyethylenesebacate, polypropylenesebacate, polybutylenesebacate and polylactic acid (PLA) as well as corresponding polyesters modified with polycarbonates or MBS. The term "polylactic acid (PLA)" designates a homopolymer of preferably poly-L-lactide and any of its blends or alloys with other polymers; a co-polymer of lactic acid or lactide with other monomers, such as hydroxy-carboxylic acids, like for example glycolic acid, 3-hydroxy-butyric acid, 4-hydroxy-butyric acid, 4-hydroxy-valeric acid, 5-hydroxy-valeric acid, 6-hydroxy-caproic acid and cyclic forms thereof; the terms "lactic acid" or "lactide" include L-lactic acid, D-lactic acid, mixtures and dimers thereof, i.e. L-lactide, D-lactide, meso-lacide and any mixtures thereof.

19. Polycarbonates and polyester carbonates.

20. Polyketones.

21. Polysulfones, polyether sulfones and polyether ketones.

22. Crosslinked polymers derived from aldehydes on the one hand and phenols, ureas and melamines on the other hand, such as phenol/formaldehyde resins, urea/formaldehyde resins and melamine/formaldehyde resins.

23. Drying and non-drying alkyd resins.

24. Unsaturated polyester resins derived from copolyesters of saturated and unsaturated dicarboxylic acids with polyhydric alcohols and vinyl compounds as crosslinking agents, and also halogen-containing modifications thereof of low flammability.

25. Crosslinkable acrylic resins derived from substituted acrylates, for example epoxy acrylates, urethane acrylates or polyester acrylates.

26. Alkyd resins, polyester resins and acrylate resins crosslinked with melamine resins, urea resins, isocyanates, isocyanurates, polyisocyanates or epoxy resins.

27. Crosslinked epoxy resins derived from aliphatic, cycloaliphatic, heterocyclic or aromatic glycidyl compounds, e.g. products of diglycidyl ethers of bisphenol A and bisphenol F, which are crosslinked with customary hardeners such as anhydrides or amines, with or without accelerators.

28. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.

29. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/PC/ABS or PBT/PET/PC.

30. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.

31. Aqueous emulsions of natural or synthetic rubber, e.g. natural latex or latices of carboxylated styrene/butadiene copolymers.

Preferred organic materials are natural, semi-synthetic or, preferably, synthetic polymers.

Particularly preferred organic materials are synthetic polymers, most preferably thermoplastic polymers. Especially preferred organic materials are polyacetals, polyolefins such as polypropylene or polyethylene, polyether/polyurethanes, polyesters such as polybutylene terephthalate, polycarbonates or vulcanisates. Particular preferred organic materials are also polyurethanes, especially those derived from hydroxyl-terminated polyethers, as well as mixtures of polyurethanes and hydroxyl-terminated polyethers. Mixtures of polyurethanes and hydroxyl-terminated polyethers occur, for example, during the preparation of polyurethanes from hydroxyl-terminated polyethers.

To be singled out for special mention is the efficacy of the compounds of the formula I against oxidative or thermal degradation, especially under the action of heat which occurs during the processing of thermoplasts and as reducers of surface energy of the organic materials. The compounds of the formula I of this invention are therefore also suited for use as processing stabilizers.

Component (b) will preferably be added to the organic material to be stabilized in concentrations of from 0.0005 to 10%, preferably 0.001 to 2%, typically 0.01 to 2%, based on the weight of said material [component (a)].

Component (b) is likewise used for polyurethane production, especially for preparing flexible polyurethane foams. In this context the novel compositions and the products produced therefrom are effectively protected against degradation. In particular, scorching during foam production is avoided.

The polyurethanes are obtained, for example, by reacting polyethers, polyesters and polybutadienes which contain terminal hydroxyl groups with aliphatic or aromatic polyisocyanates.

Polyethers having terminal hydroxyl groups are known and are prepared, for example, by polymerizing epoxides such as ethylene oxide, propylene oxide, butylene oxide, tetrahydrofuran, styrene oxide or epichlorohydrin with themselves, for example in the presence of $BF_3$, or by addition reaction of these epoxides, alone or as a mixture or in succession, with starting components containing reactive hydrogen atoms, such as water, alcohols, ammonia or amines, for example ethylene glycol, propylene 1,3- and 1,2-glycol, trimethylolpropane, 4,4'-dihydroxydiphenylpropane, aniline, ethanolamine or ethylenediamine. Sucrose polyethers are also suitable in accordance with the invention. In many cases preference is given to those polyethers which predominantly (up to 90% by weight, based on all the OH groups present in the polyether) contain primary OH groups. Furthermore, polyethers modified by vinyl polymers, as are formed, for example, by polymerizing styrene and acrylonitrile in the presence of polyethers, are suitable, as are polybutadienes containing OH groups.

These compounds generally have molecular weights of 400-10000 and are polyhydroxy compounds, especially compounds containing from two to eight hydroxyl groups, especially those of molecular weight from 800 to 10 000, preferably from 1000 to 6000, for example polyethers containing at least 2, generally 2 to 8, but preferably 2 to 4, hydroxyl groups, as are known per se for the preparation of homogeneous polyurethanes and cellular polyurethanes.

It is of course possible to employ mixtures of the above compounds containing at least two isocyanate-reactive hydrogen atoms, in particular with a molecular weight of 400-10 000.

Suitable polyisocyanates are aliphatic, cycloaliphatic, araliphatic, aromatic and heterocyclic polyisocyanates, for example ethylene diisocyanate, 1,4-tetramethylene diisocyanate, 1,6-hexamethylene diisocyanate, 1,12-dodecane diisocyanate, cyclobutane 1,3-diisocyanate, cyclohexane 1,3- and -1,4-diisocyanate and also any desired mixtures of these isomers, 1-isocyanato-3,3,5-trimethyl-5-isocyanatomethylcyclohexane, 2,4- and 2,6-hexahydrotolylene diisocyanate and also any desired mixtures of these isomers, hexahydro-1,3- and/or -1,4-phenylene diisocyanate, perhydro-2,4'- and/or -4,4'-diphenylmethanediisocyanate, 1,3- and 1,4-phenylene diisocyanate, 2,4- and 2,6-tolylene diisocyanate, and also any desired mixtures of these isomers, diphenylmethane 2,4'- and/or -4,4'-diisocyanate, naphthylene 1,5-diisocyanate, triphenylmethane 4,4',4''-triisocyanate, polyphenyl-polymethylene polyisocyanates as are obtained by aniline-formaldehyde condensation followed by phosgenization, m- and p-isocyanatophenylsulfonyl isocyanates, perchlorinated aryl polyisocyanates, polyisocyanates containing carbodiimide groups, polyisocyanates containing allophanate groups, polyisocyanates containing isocyanurate groups, polyisocyanates containing urethane groups, polyisocyanates containing acylated urea groups, polyisocyanates containing biuret groups, polyisocyanates containing ester groups, reaction products of the abovementioned isocyanates with acetals, and polyisocyanates containing polymeric fatty acid radicals.

It is also possible to employ the isocyanate group-containing distillation residues, as they are or dissolved in one or more of the abovementioned polyisocyanates, which are obtained in the course of the industrial preparation of isocyanates. It is additionally possible to use any desired mixtures of the abovementioned polyisocyanates.

Particular preference is given in general to the polyisocyanates which are readily obtainable industrially, for example 2,4- and 2,6-tolylene diisocyanate and any desired mixtures of these isomers ("TDI"), polyphenyl-polymethylene-polyisocyanates as prepared by aniline-formaldehyde condensation followed by phosgenization ("crude MDI"), and polyisocyanates containing carbodiimide, urethane, allophanate, isocyanurate, urea or biuret groups ("modified polyisocyanates").

Component (b) is also suitable for stabilizing polyolefins which are in long-term contact with extracting media.

In addition to components (a) and (b) the novel compositions may comprise further costabilizers (additives), typically the following:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example 2,6-di-nonyl-4-methylphenol, 2,4-dimethyl-6-(1'-methylundec-1-yl)phenol, 2,4-dimethyl-6-(1-methylheptadec-1'-yl) phenol, 2,4-dimethyl-6-(1'-methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis (3,5-di-tert-butyl-4-hydroxyphenyl)adipate.

1.4. Tocopherols, for example α-tocopherol, β-tocopherol, γ-tocopherol, δ-tocopherol and mixtures thereof (vitamin E).

1.5. Hydroxylated thiodiphenyl ethers, for example 2, 2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis(3,6-di-sec-amylphenol), 4,4'-bis(2,6-dimethyl-4-hydroxyphenyl) disulfide.

1.6. Alkylidenebisphenols, for example 2, 2'-methylenebis (6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl)butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis(3,5-di-tert-butyl-4-hydroxyphenyl)propane, 2,2-bis-(5-tert-butyl-4-hydroxy2-methylphenyl)-4-n-dodecylmercaptobutane, 1,1,5,5-tetra(5-tert-butyl-4-hydroxy-2-methylphenyl)pentane.

1.7. O-, N- and S-benzyl compounds, for example 3, 5,3',5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzyl mercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5-di-tert-butyl-4-hydroxybenzylmercaptoacetate.

1.8. Hydroxybenzylated malonates, for example dioctadecyl-2,2-bis(3,5-di-tert-butyl-2-hydroxybenzyl)malonate, di-octadecyl-2-(3-tert-butyl-4-hydroxy-5-methylbenzyl)malonate, di-dodecylmercaptoethyl-2,2-bis(3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl) malonate.

1.9. Aromatic hydroxybenzyl compounds, for example 1,3,5-tris(3,5-di-tert-butyl-4-hydroxybenzyl)-2,4,6-trimethylbenzene, 1,4-bis(3,5-di-tert-butyl-4-hydroxybenzyl)-2,3,5,6-tetramethyl benzene, 2,4,6-tris(3,5-di-tert-butyl-4-hydroxybenzyl)phenol.

1.10. Triazine compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris(3,5-di-tert-butyl-4-hydroxybenzyl)isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.11. Benzylphosphonates, for example dimethyl-2,5-di-tert-butyl-4-hydroxybenzylphosphonate, diethyl-3,5-di-tert-butyl-4-hydroxybenzyl phosphonate, dioctadecyl-3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(5-tert-butyl-4-hydroxy-3-methylphenyl) propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane; 3,9-bis[2-{3-(3-tert-butyl-4-hydroxy-5-methylphenyl)propionyloxy}-1,1-dimethylethyl]-2,4,8,10-tetraoxaspiro[5.5]undecane.

1.15. Esters of β-(3,5-dicyclohexyl-4-hydroxyphenyl)propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl) propionic acid e.g. N,N'-bis(3,5-di-tert-butyl-4-hydroxyphenylpropionyl)hexamethylenediamide, N,N'-bis(3,5-di-tert-butyl-4-hydroxyphenylpropionyl)trimethylenediamide, N,N'-bis(3,5-di-tert-butyl-4-hydroxyphenylpropionyl)hydrazide, N,N'-bis[2-(3-[3,5-di-tert-butyl-4-hydroxyphenyl]propionyloxy)ethyl]oxamide (Naugard®XL-1, supplied by Uniroyal).

1.18. Ascorbic acid (vitamin C)

1.19. Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylamino-methylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino]

ethane, 1,2-bis(phenylamino)propane, (o-tolyl)biguanide, bis[4-(1,3'-dimethylbutyl)phenyl]amine, tert-octylated N-phenyl-1-naphthylamine, a mixture of mono- and dialkylated tert-butyl/tert-octyldiphenylamines, a mixture of mono- and dialkylated nonyldiphenylamines, a mixture of mono- and dialkylated dodecyldiphenylamines, a mixture of mono- and dialkylated isopropyl/isohexyldiphenylamines, a mixture of mono- and dialkylated tert-butyldiphenylamines, 2,3-dihydro-3,3-dimethyl-4H-1,4-benzothiazine, phenothiazine, a mixture of mono- and dialkylated tert-butyl/tert-octylphenothiazines, a mixture of mono- and dialkylated tert-octylphenothiazines, N-allylphenothiazine, N,N,N',N'-tetraphenyl-1,4-diaminobut-2-ene, N,N-bis(2,2,6,6-tetramethylpiperid-4-yl-hexamethylenediamine, bis(2,2,6,6-tetramethylpiperid-4-yl)sebacate, 2,2,6,6-tetramethylpiperidin-4-one, 2,2,6,6-tetramethylpiperidin-4-ol.

2. UV Absorbers and Light Stabilizers 2.1. 2-(2'-Hydroxyphenyl)benzotriazoles, for example 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chlorobenzotriazole, 2-(3'-tert-butyl-2'-hydroxy-5'-methylphenyl)-5-chlorobenzotriazole, 2-(3'-sec-butyl-5'-tert-butyl-2'-hydroxyphenyl)benzotriazole, 2-(2'-hydroxy-4'-octyloxyphenyl)benzotriazole, 2-(3',5'-di-tert-amyl-2'-hydroxyphenyl)benzotriazole, 2-(3',5'-bis(α,α-dimethylbenzyl)-2'-hydroxyphenyl)benzotriazole, 2-(3'-tert-butyl-2'-hydroxy-5'-(2-octyloxycarbonylethyl)phenyl)-5-chlorobenzotriazole, 2-(3'-tert-butyl-5'-[2-(2-ethylhexyloxy)carbonylethyl]-2'-hydroxyphenyl)-5-chlorobenzotriazole, 2-(3'-tert-butyl-2'-hydroxy-5'-(2-methoxycarbonylethyl)phenyl)-5-chlorobenzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole, 2-(3'-tert-butyl-2'-hydroxy-5'-(2-isooctyloxycarbonylethyl)phenylbenzotriazole, 2,2'-methylenebis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl)-2H-benzotriazole with polyethylene glycol 300; [R—CH$_2$CH$_2$—COO—CH$_2$CH$_2$—]$_2$, where R=3'-tert-butyl-4'-hydroxy-5'-2H-benzotriazol-2-ylphenyl, 2-[2'-hydroxy-3'-(α,α-dimethylbenzyl)-5'-(1,1,3,3-tetramethylbutyl)phenyl]benzotriazole; 2-[2'-hydroxy-3'-(1,1,3,3-tetramethylbutyl)-5'-(α,α-dimethylbenzyl)phenyl]benzotriazole.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy benzophenone derivatives.

2.3. Esters of substituted and unsubstituted benzoic acids, for example 4-tert-butylphenyl salicylate, phenyl salicylate, octylphenyl salicylate, dibenzoyl resorcinol, bis(4-tert-butylbenzoyl)resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxycinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thiobis[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenylundecylketoxime, nickel complexes of 1-phenyl-4-lauroyl-5-hydroxypyrazole, with or without additional ligands.

2.6. Sterically hindered amines, for example bis(2,2,6,6-tetramethyl-4-piperidyl)sebacate, bis(2,2,6,6-tetramethyl-4-piperidyl)succinate, bis(1,2,2,6,6-pentamethyl-4-piperidyl)sebacate, bis(1-octyloxy-2,2,6,6-tetramethyl-4-piperidyl)sebacate, bis(1,2,2,6,6-pentamethyl-4-piperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl)nitrilotriacetate, tetrakis(2,2,6,6-tetramethyl-4-piperidyl)-1,2,3,4-butanetetracarboxylate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decane-2,4-dione, bis(1-octyloxy-2,2,6,6-tetramethylpiperidyl)sebacate, bis(1-octyloxy-2,2,6,6-tetramethylpiperidyl)succinate, linear or cyclic condensates of N,N'-bis(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidine-2,5-dione, 3-dodecyl-1-(1,2,2,6,6-pentamethyl-4-piperidyl)pyrrolidine-2,5-dione, a mixture of 4-hexadecyloxy- and 4-stearyloxy-2,2,6,6-tetramethylpiperidine, a condensate of N,N'-bis(2,2,6,6-tetramethyl-4-piperidyl)hexamethylenediamine and 4-cyclohexylamino-2,6-dichloro-1,3,5-triazine, a condensate of 1,2-bis(3-aminopropylamino)ethane and 2,4,6-trichloro-1,3,5-triazine as well as 4-butylamino-2,2,6,6-tetramethylpiperidine (CAS Reg. No. [136504-96-6]); a condensate of 1,6-hexanediamine and 2,4,6-trichloro-1,3,5-triazine as well as N,N-dibutylamine and 4-butylamino-2,2,6,6-tetramethylpiperidine (CAS Reg. No. [192268-64-7]); N-(2,2,6,6-tetramethyl-4-piperidyl)-n-dodecylsuccinimide, N-(1,2,2,6,6-pentamethyl-4-piperidyl)-n-dodecylsuccinimide, 2-undecyl-7,7,9,9-tetramethyl-1-oxa-3,8-diaza-4-oxospiro[4,5]decane, a reaction product of 7,7,9,9-tetramethyl-2-cycloundecyl-1-oxa-3,8-diaza-4-oxospiro-[4,5]decane and epichlorohydrin, 1,1-bis(1,2,2,6,6-pentamethyl-4-piperidyloxycarbonyl)-2-(4-methoxyphenyl)ethene, N,N'-bisformyl-N,N'-bis(2,2,6,6-tetramethyl-4-piperidyl)hexamethylenediamine, a diester of 4-methoxymethylenemalonic acid with 1,2,2,6,6-pentamethyl-4-hydroxypiperidine, poly[methylpropyl-3-oxy-4-(2,2,6,6-tetramethyl-4-piperidyl)]siloxane, a reaction product of maleic acid anhydride-α-olefin copolymer with 2,2,6,6-tetramethyl-4-aminopiperidine or 1,2,2,6,6-pentamethyl-4-aminopiperidine.

2.7. Oxamides, for example 4, 4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1, 3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxypropoxy)phenyl]-4, 6-bis(2,4-dimethyl)-1,3,5-triazine, 2-[2-hydroxy-4-(2-hydroxy-3-octyloxypropyloxy)phenyl]-4,6-bis(2,4-dimethyl)-1,3,5-triazine, 2-[4-(dodecyloxy/tridecyloxy-2-hydroxypropoxy)-2-hydroxyphenyl]-4,6-bis(2,4-dimethylphenyl)-1,3,5-triazine, 2-{2-hydroxy-4-(2-hydroxy-3-dodecyloxypropoxy)phenyl}-4,6-bis(2,4-dimethylphenyl)-1,3,5-triazine, 2-(2-hydroxy-4-hexyloxy) phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxypropoxy)phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxypropyloxy]phenyl}-4,6-bis(2,4-dimethylphenyl)-1,3,5-triazine.

2.9. N-alkyl-N,N'-diarylformamidines, for example, benzoic acid, 4-[[(methylphenylamino)methylene]amino]ethyl ester [for example: Tinuvin® 101 supplied by Ciba Specialty Chemicals Inc.]; benzoic acid, 4-[[(ethylphenylamino)methylene]amino]ethyl ester; 2-propenoic acid, 3-(4-methoxyphenyl)-, 2-ethylhexyl ester [for example: Uvinul® 3088 supplied by BASF]; 2-propenoic acid, 2-cyano-3,3-diphenyl-, ethyl ester [for example: Uvinul® 3035 supplied by BASF]; or 2-propenoic acid, 2-cyano-3,3-diphenyl-, 2-ethylhexyl ester [for example: Uvinul® 3039 suppied by BASF].

3. Metal deactivators, for example N,N'-diphenyloxamide, N-salicylal-N'-salicyloyl hydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl)oxalyldihydrazide, N,N'-bis(salicyloyl)thiopropionyl dihydrazide.

4. Phosphites and phosphonites, for example triphenyl phosphite, diphenylalkyl phosphites, phenyldialkyl phosphites, tris(nonylphenyl)phosphite, trilauryl phosphite, trioctadecyl phosphite, distearylpentaerythritol diphosphite, tris(2, 4-di-tert-butylphenyl)phosphite, diisodecyl pentaerythritol diphosphite, bis(2,4-di-tert-butylphenyl)pentaerythritol diphosphite, bis(2,4-di-cumylphenyl)pentaerythritol diphosphite, bis(2,6-di-tert-butyl-4-methylphenyl)pentaerythritol diphosphite, diisodecyloxypentaerythritol diphosphite, bis (2,4-di-tert-butyl-6-methylphenyl)pentaerythritol diphosphite, bis(2,4,6-tris(tert-butylphenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz[d,g]-1,3,2-dioxaphosphocin, bis(2,4-di-tert-butyl-6-methylphenyl) methyl phosphite, bis(2,4-di-tert-butyl-6-methylphenyl) ethyl phosphite, 6-fluoro-2,4,8,10-tetra-tert-butyl-[2-methyl-dibenz[d,g]-1,3,2-dioxaphosphocin, 2,2',2"-nitrilo-[triethyltris(3,3',5,5'-tetra-tert-butyl-1,1'-biphenyl-2,2'-diyl) phosphite], 2-ethylhexyl(3,3',5,5'-tetra-tert-butyl-1,1'-biphenyl-2,2'-diyl)phosphite, 5-butyl-5-ethyl-2-(2,4,6-tri-tert-butylphenoxy)-1,3,2-dioxaphosphirane.

5. Hydroxylamines, for example N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

6. Nitrones, for example N-benzyl-alpha-phenylnitrone, N-ethyl-alpha-methylnitrone, N-octyl-alpha-heptylnitrone, N-lauryl-alpha-undecylnitrone, N-tetradecyl-alpha-tridecylnitrone, N-hexadecyl-alpha-pentadecylnitrone, N-octadecyl-alpha-heptadecylnitrone, N-hexadecyl-alpha-heptadecylnitrone, N-ocatadecyl-alpha-pentadecylnitrone, N-heptadecyl-alpha-heptadecylnitrone, N-octadecyl-alpha-hexadecylnitrone, nitrone derived from N,N-dialkylhydroxylamine derived from hydrogenated tallow amine.

7. Thiosynergists, for example dilauryl thiodipropionate or distearyl thiodipropionate.

8. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

9. Polyamide stabilizers, for example copper salts in combination with iodides and/or phosphorus compounds and salts of divalent manganese.

10. Basic co-stabilizers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example calcium stearate, zinc stearate, magnesium behenate, magnesium stearate, sodium ricinoleate and potassium palmitate, antimony pyrocatecholate or zinc pyrocatecholate.

11. Nucleating agents, for example inorganic substances, such as talcum, metal oxides, such as titanium dioxide or magnesium oxide, phosphates, carbonates or sulfates of, preferably, alkaline earth metals; organic compounds, such as mono- or polycarboxylic acids and the salts thereof, e.g. 4-tert-butylbenzoic acid, adipic acid, diphenylacetic acid, sodium succinate or sodium benzoate; polymeric compounds, such as ionic copolymers (ionomers). Especially preferred are 1,3:2,4-bis(3',4'-dimethylbenzylidene)sorbitol, 1,3:2,4-di(paramethyldibenzylidene)sorbitol, 1,3:2,4-di (benzylidene)sorbitol and Irgaclear XT386 (®, Ciba Inc.).

12. Fillers and reinforcing agents, for example calcium carbonate, silicates, glass fibres, glass bulbs, asbestos, talc, kaolin, mica, barium sulfate, metal oxides and hydroxides, carbon black, graphite, wood flour and flours or fibers of other natural products, synthetic fibers.

13. Other additives, for example plasticisers, lubricants, emulsifiers, pigments, rheology additives, catalysts, flow-control agents, optical brighteners, flameproofing agents, antistatic agents and blowing agents.

14. Benzofuranones and indolinones, for example those disclosed in U.S. Pat. No. 4,325,863; U.S. Pat. No. 4,338,244; U.S. Pat. No. 5,175,312; U.S. Pat. No. 5,216,052; U.S. Pat. No. 5,252,643; DE-A-4316611; DE-A-4316622; DE-A-4316876; EP-A-0589839, EP-A-0591102; EP-A-1291384 or 3-[4-(2-acetoxyethoxy)phenyl]-5,7-di-tert-butyl benzofuran-2-one, 5,7-di-tert-butyl-3-[4-(2-stearoyl-oxyethoxy)phenyl]benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butylbenzofuran-2-one, 3-(3,5-dimethyl-4-pivaloyloxyphenyl)-5,7-di-tert-butylbenzofuran-2-one, 3-(3,4-dimethylphenyl)-5,7-di-tert-butylbenzofuran-2-one, 3-(2,3-dimethylphenyl)-5,7-di-tert-butyl benzofuran-2-one, 3-(2-acetyl-5-isooctylphenyl)-5-iso-octylbenzofuran-2-one.

The costabilizers are added, for example, in concentrations of from 0.01 to 10%, based on the overall weight of the organic material to be stabilized.

The compounds of the formula I can be used in particular together with phenolic antioxidants, light stabilizers and/or processing stabilizers.

Other preferred compositions comprise, in addition to compounds of the formula I, a compound of the organic phosphite or phosphonite type.

The fillers and reinforcing agents (item 12 in the list), for example talc, calcium carbonate, mica or kaolin, are added to the polyolefin in concentrations, for example, of from 0.01 to 40%, based on the organic material to be stabilized.

Further preferred compositions comprise in addition to components (a) and (b) further additives as well, especially alkaline earth metal salts of higher fatty acids, for example calcium stearate, calcium lactate and/or calcium stearoyl-2-lactylate.

As a conventional stabilizer combination for the processing of polymeric organic materials, such as, for example, polyolefins, into corresponding moulded articles, the combination of a phenolic antioxidant with a secondary antioxidant based on an organic phosphite or phosphonite is recommended. Depending on the substrate and process, however, many polyolefin processors are obliged to operate processes in the high-temperature range above approx. 280° C. The inclusion of a processing stabilizer of the formula I is particularly suitable for high-temperature applications, especially in the temperature range above 300° C. Technical materials and moulded articles for instance based on HD polyethylene, such as, for example, pipes and their technical variants (fittings), can be manufactured with a higher output and fewer rejects. A further advantage of the compounds of the formula I is also that they can be used in a very small amount, which results in a reduction in the overall antioxidant concentration compared with conventional stabilizer mixtures. For instance the use of a low concentration of a compound of the formula I allows the overall stabilizer concentration to be reduced by approximately a third in, for example, polyolefins, which at the same time represents an economic advantage.

The compounds of the formula I and other optional additives are incorporated into the organic polymeric material according to known methods, for example before or during shaping to moulded articles or alternatively by coating the organic polymeric material with a solution or dispersion of the compounds and subsequently evaporating the solvent. The compounds of the formula I can also be added to the materials to be stabilized in the form of a master batch which contains these compounds, typically in a concentration of, for example, from 2.5 to 25% by weight.

The compounds of the formula I may also be added before or during polymerization or before crosslinking.

The compounds of the formula I, and where applicable further additives, may be incorporated into the material to be stabilized in pure form or encapsulated in waxes, oils or polymers.

The compounds of the formula I, and where applicable further additives, may also be sprayed onto the polymer to be stabilized. They are able to be used to dilute other additives (e.g. the above-mentioned conventional additives) or melts thereof, so that they can also be sprayed together with these additives onto the polymer to be stabilized. Application by spraying during the deactivation of the polymerization catalysts is especially advantageous, in which case spraying is conveniently effected with the vapour used for deactivation.

The materials stabilized in this way can be employed in a wide variety of forms, for example as films, fibres, tapes, moulding compositions, profiles or as binders for coating materials, especially powder coatings, adhesives or putties.

The polyolefins stabilized in this way can likewise be employed in a wide variety of forms, especially as thick-layer polyolefin mouldings which are in long-term contact with extractive media, such as, for example pipes for liquids or gases, films, geomembranes, tapes, strips, profiles or tanks.

The preferred thick-layer polyolefin mouldings have a layer thickness of from 1 to 50 mm, in particular from 1 to 30 mm, for example from 2 to 10 mm.

Preference is given to a process for stabilizing polyolefins that are in long-term contact with extractive media, wherein the polyolefins are thick-layer polyolefin mouldings and have a layer thickness of from 1 to 50 mm, in particular from 1 to 30 mm, for example from 2 to 10 mm, which comprises incorporating in or applying to said polyolefins at least a compound of the formula I.

Also of particular interest is a process for stabilizing thick-layer polyolefin mouldings that are in long-term contact with extractive media, wherein the thick-layer polyolefin mouldings are pipes or geomembranes, which comprises incorporating in or applying to said mouldings at least a compound of the formula I.

The term geomembranes refers to films which are employed, for example, in landfill sites and are required to have a service life of up to 300 years.

Extractive media are, for example, liquid or gaseous inorganic or organic materials.

Examples of gaseous inorganic materials are oxygen; nitrogen; oxides of nitrogen; for example NO, laughing gas or $NO_2$; oxides of sulfur, for example sulfur dioxide; halogens, for example fluorine or chlorine; Brönstedt acids, for example hydrofluoric acid, hydrochloric acid, hydrobromic acid, hydroiodic acid or hydrocyanic acid; or bases, for example ammonia.

Examples of gaseous organic materials are $C_1$-$C_4$alkanes, for example methane, ethane, propane or butane; carbon monoxide; carbon dioxide; or phosgene.

Examples of liquid inorganic materials are water, chlorinated drinking water or aqueous salt solutions, for example sodium chloride solution (brine) or sodium sulfate solution; bromine; acid halides, e.g. titanium tetrachloride, thionyl chloride, nitrosyl chloride or trimethylsilyl chloride; alkalis, for example aqueous sodium hydroxide (NaOH), aqueous potassium hydroxide (KOH), aqueous ammonia solution, aqueous sodium bicarbonate solution or aqueous sodium carbonate solution.

Examples of liquid organic materials are organic solvents or liquid organic reagents.

Examples of organic solvents are aliphatic hydrocarbons, for example pentane, hexane, heptane, octane, petroleum spirit, nonane or decane; alcohols, for example methanol, ethanol, isopropanol, butanol, pentanol, amyl alcohol, cyclohexanol, pentaerythritol, ethylene glycol, ethylene diglycol, methylcellosolve, polyethylene glycol or glycerol; ketones, for example acetone, diethyl ketone, methyl ethyl ketone, diphenyl ketone or cyclohexanone; ethers, for example diethyl ether, dibutyl ether, tetrahydrofuran or dioxane; aromatic hydrocarbons, for example benzene, toluene or xylene; heterocyclic solvents, for example furan, pyridine, 2,6-lutidine or thiophene; dipolar aprotic solvents, for example dimethylformamide, diethylacetamide or acetonitrile; or surfactants.

For the purposes of the present invention, extractive media are also mixtures and solutions, especially aqueous mixtures, emulsions or solutions, of liquid or gaseous inorganic and organic materials as listed above.

Of particular interest are those extractive media which are important in the chemical industry or in landfill sites.

The present invention relates also to new compounds of the formula I

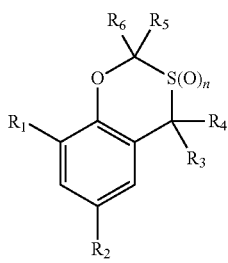

wherein
$R_1$ and $R_2$ independently of each other are hydrogen, $C_1$-$C_{25}$alkyl, $C_2$-$C_{25}$alkenyl, unsubstituted or with $C_1$-$C_4$alkyl substituted phenyl; unsubstituted or with $C_1$-$C_4$alkyl substituted $C_7$-$C_9$phenylalkyl; —CH($R_7$)—S(O)$_n$—$R_8$ or —CH($R_7$)—S(O)$_n$—CH$_2$—CH($R_7$)—$R_9$, $R_3$ and $R_4$ independently of each other are hydrogen, $C_1$-$C_{25}$alkyl, unsubstituted or with $C_1$-$C_4$alkyl substituted phenyl, $R_5$ and $R_6$ independently of each other are hydrogen, $C_1$-$C_{25}$alkyl, $C_2$-$C_{25}$alkyl interrupted by oxygen; unsubstituted or with $C_1$-$C_4$alkyl substituted phenyl; halogen, —CN, —NO$_2$,

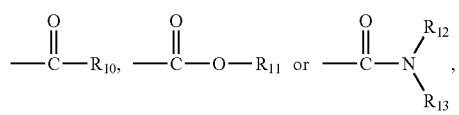

$R_7$ is hydrogen, $C_1$-$C_{12}$alkyl,

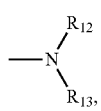

unsubstituted or with halogen or $C_1$-$C_4$alkyl substituted phenyl;

$R_8$ is a monovalent perfluorinated alkyl or alkenyl, linear or branched organic radical having four to twenty fully fluorinated carbon atoms, $R_9$ is —CN, —S(O)$_n$—$R_{10}$,

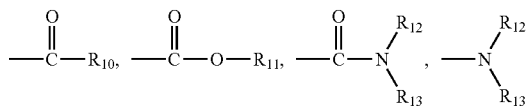

or —NO$_2$, $R_{10}$ is hydrogen, $C_1$-$C_{25}$alkyl, $C_7$-$C_9$phenylalkyl, unsubstituted or $C_1$-$C_4$alkyl-substituted phenyl; unsubstituted or $C_1$-$C_4$alkyl-substituted $C_5$-$C_8$cycloalkyl;

$R_{11}$ is hydrogen, alkali metal, $C_1$-$C_{25}$alkyl, $C_7$-$C_9$phenylalkyl, unsubstituted or $C_1$-$C_4$alkyl-substituted phenyl; unsubstituted or $C_1$-$C_4$alkyl-substituted $C_5$-$C_8$cycloalkyl; or $C_3$-$C_{25}$alkyl which is interrupted by oxygen or sulfur;

$R_{12}$ and $R_{13}$ independently of one another are hydrogen, $C_1$-$C_{25}$alkyl, $C_1$-$C_4$alkanoyl, $C_7$-$C_9$-phenylalkyl, unsubstituted or $C_1$-$C_4$alkyl-substituted phenyl; or $R_{12}$ and $R_{13}$, together with the nitrogen atom to which they are attached, form a 5-, 6- or 7-membered heterocyclic ring which is unsubstituted or is substituted by $C_1$-$C_4$alkyl or is interrupted by oxygen, sulfur or

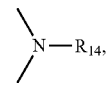

$R_{14}$ is hydrogen, $C_1$-$C_8$alkyl or benzyl, and
n is 0, 1 or 2.

The preferred general symbols are identical to those of the compounds of the formula I disclosed in the composition with an organic material.

Of special interest are the compounds of the formula I wherein
$R_1$ is $C_1$-$C_4$alkyl, —CH($R_7$)—S(O)$_n$—$R_8$ or —CH($R_7$)—S(O)$_n$—CH$_2$—CH($R_7$)—$R_9$,
$R_2$ is $C_1$-$C_4$alkyl, —CH($R_7$)—S(O)$_n$—$R_8$ or —CH($R_7$)—S(O)$_n$—CH$_2$—CH($R_7$)—$R_9$,
$R_3$ is hydrogen,
$R_4$ is hydrogen or phenyl,
$R_5$ is hydrogen,
$R_6$ is hydrogen or phenyl,
$R_7$ is hydrogen,
$R_8$ is —CH$_2$—CH$_2$—(CF$_2$)$_3$CF$_3$ or —CH$_2$—CH$_2$—(CF$_2$)$_7$CF$_3$,
$R_9$ is

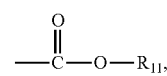

$R_{11}$ is hydrogen or $C_1$-$C_8$alkyl, and
n is 0, 1 or 2.

The compounds of the formula I are prepared from the corresponding phenols (see Table 2).

For example, the compounds of formula Ia

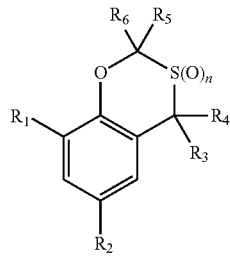
(Ia)

wherein
$R_1$ and $R_2$ independently of each other are hydrogen, $C_1$-$C_{25}$alkyl, $C_2$-$C_{25}$alkenyl, unsubstituted or with $C_1$-$C_4$alkyl substituted phenyl; unsubstituted or with $C_1$-$C_4$alkyl substituted $C_7$-$C_9$phenylalkyl; —CH($R_7$)—S(O)$_n$—$R_8$ or —CH($R_{7a}$)—S(O)$_n$—CH$_2$—CH($R_{7b}$)—$R_9$,
$R_3$ is H,
$R_4$ is hydrogen, $C_1$-$C_{12}$alkyl, unsubstituted or with $C_1$-$C_4$alkyl substituted phenyl,
$R_5$ and $R_6$ independently of each other are hydrogen, $C_1$-$C_{25}$alkyl, $C_2$-$C_{25}$alkyl interrupted by oxygen; unsubstituted or with $C_1$-$C_4$alkyl substituted phenyl; halogen, —CN, —NO$_2$,

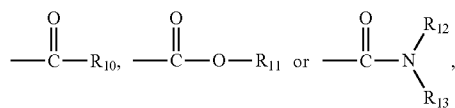

$R_7$, $R_{7a}$ and $R_{7b}$ independently of each other are hydrogen, $C_1$-$C_{12}$alkyl, unsubstituted or with $C_1$-$C_4$alkyl substituted phenyl;
$R_8$ is a monovalent perfluorinated alkyl or alkenyl, linear or branched organic radical having four to twenty fully fluorinated carbon atoms,
$R_9$ is —CN, —S(O)$_n$—$R_{10}$,

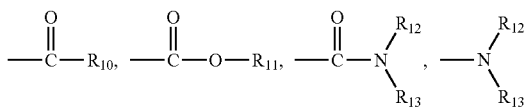

or —NO$_2$,
$R_{10}$ is hydrogen, $C_1$-$C_{25}$alkyl, $C_7$-$C_9$phenylalkyl, unsubstituted or $C_1$-$C_4$alkyl-substituted phenyl; unsubstituted or $C_1$-$C_4$alkyl-substituted $C_5$-$C_8$cycloalkyl;
$R_{11}$ is hydrogen, alkali metal, $C_1$-$C_{25}$alkyl, $C_7$-$C_9$phenylalkyl, unsubstituted or $C_1$-$C_4$alkyl-substituted phenyl; unsubstituted or $C_1$-$C_4$alkyl-substituted $C_5$-$C_8$cycloalkyl; or $C_3$-$C_{25}$alkyl which is interrupted by oxygen or sulfur;
$R_{12}$ and $R_{13}$ independently of one another are hydrogen, $C_1$-$C_{25}$alkyl, $C_1$-$C_4$alkanoyl, $C_7$-$C_9$-phenylalkyl, unsubstituted or $C_1$-$C_4$alkyl-substituted phenyl; or $R_{12}$ and $R_{13}$, together with the nitrogen atom to which they are attached, form a 5-, 6- or 7-membered heterocyclic ring which is unsubstituted or is substituted by $C_1$-$C_4$alkyl or is interrupted by oxygen, sulfur or

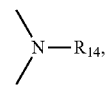

$R_{14}$ is hydrogen, $C_1$-$C_8$alkyl or benzyl, and
n is 0,
can be prepared by a process, which comprises the step of reacting a compound of formula II

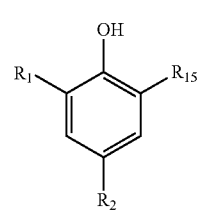
(II)

wherein
$R_1$ and $R_2$ have the meaning as indicated for the compound of formula Ia,
$R_{15}$ is —CH($R_{7a}$)—S(O)$_n$—CH$_2$—CH($R_{7b}$)—$R_9$,
$R_7$, $R_{7a}$ and $R_{7b}$ and $R_9$ have the meaning as indicated for the compound of formula Ia
with a compound of formula IIII $$CXYR_5R_6 \qquad (III),$$

wherein $R_5$ and $R_6$ have the meaning as indicated for the compound of formula Ia, and X and Y independently of each other are halogen.

Halogen can be fluorine, chlorine, bromine or iodine. Chlorine and iodine are the preferred halogens. Examples of compounds of formula III are diiodomethane and benzal chloride.

Preferably, the molar ratio of the compound of formula III/compound of formula II is 1/1 to 10/1, more preferably 3/1 to 7/1 and most preferably 4.5/1 to 5.5/1.

Preferably the reaction of the compound of formula II with the compound of formula III takes place in the presence of a base. Examples of bases are alkali metal hydroxide such as sodium hydroxide, alkali metal and earth alkaline metal carbonates such as calcium carbonate and ammonia. Preferably, sodium hydroxide is used.

Preferably, the molar ratio of the compound of the base/compound of formula II is 1/1 to 10/1, more preferably 3/1 to 7/1 and most preferably 4.5/1 to 5.5/1.

The reaction is usually carried out in a solvent. The solvent is preferably in polar and aprotic organic solvent such as sulfolane, 1-methyl-2-pyrrolidone, N,N-dimethylacetamide, paraformamide and N,N-dimethylformamide. Sulfolane is the preferred solvent.

The reaction is usually performed at a temperature of 10 to 40° C., preferably from 15 to 30° C., more preferably from 20 to 25° C.

The compound of formula Ia can be isolated from the reaction mixture, for example by chromatography or crystallization.

For example, the compounds of formula Ib

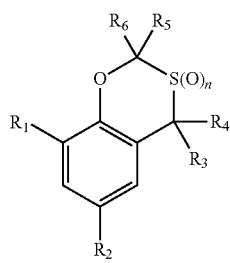
(Ib)

wherein
$R_1$ and $R_2$ independently of each other are hydrogen, $C_1$-$C_{25}$alkyl, $C_2$-$C_{25}$alkenyl, unsubstituted or with $C_1$-$C_4$alkyl substituted phenyl; unsubstituted or with $C_1$-$C_4$alkyl substituted $C_7$-$C_9$phenylalkyl; —CH($R_7$)—S(O)$_n$—$R_8$ or —CH($R_7$)—S(O)$_n$—CH$_2$—CH($R_{7b}$)—$R_9$,
$R_3$ and $R_4$ independently of each other are hydrogen, $C_1$-$C_{25}$alkyl, unsubstituted or with $C_1$-$C_4$alkyl substituted phenyl,
$R_5$ and $R_6$ independently of each other are hydrogen, $C_1$-$C_{25}$alkyl, $C_2$-$C_{25}$alkyl interrupted by oxygen; unsubstituted or with $C_1$-$C_4$alkyl substituted phenyl; halogen, —CN, —NO$_2$,

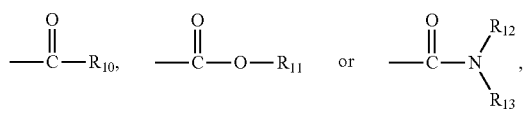

$R_7$, $R_{7a}$ and $R_{7b}$ independently of each other are hydrogen, $C_1$-$C_{12}$alkyl,

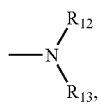

unsubstituted or with halogen or $C_1$-$C_4$alkyl substituted phenyl;
$R_8$ is a monovalent perfluorinated alkyl or alkenyl, linear or branched organic radical having four to twenty fully fluorinated carbon atoms,
$R_9$ is —CN, —S(O)$_n$—$R_{10}$,

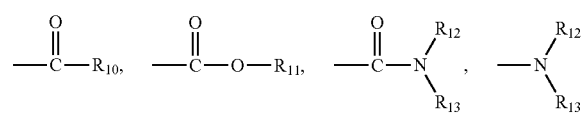

or —NO$_2$,
$R_{10}$ is hydrogen, $C_1$-$C_{25}$alkyl, $C_7$-$C_9$phenylalkyl, unsubstituted or $C_1$-$C_4$alkyl-substituted phenyl; unsubstituted or $C_1$-$C_4$alkyl-substituted $C_5$-$C_8$cycloalkyl;
$R_{11}$ is hydrogen, alkali metal, $C_1$-$C_{25}$alkyl, $C_7$-$C_9$phenylalkyl, unsubstituted or $C_1$-$C_4$alkyl-substituted phenyl; unsubstituted or $C_1$-$C_4$alkyl-substituted $C_5$-$C_8$cycloalkyl; or $C_3$-$C_{25}$alkyl which is interrupted by oxygen or sulfur;

$R_{12}$ and $R_{13}$ independently of one another are hydrogen, $C_1$-$C_{25}$alkyl, $C_1$-$C_4$alkanoyl, $C_7$-$C_9$-phenylalkyl, unsubstituted or $C_1$-$C_4$alkyl-substituted phenyl; or $R_{12}$ and $R_{13}$, together with the nitrogen atom to which they are attached, form a 5-, 6- or 7-membered heterocyclic ring which is unsubstituted or is substituted by $C_1$-$C_4$alkyl or is interrupted by oxygen, sulfur or

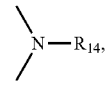

$R_{14}$ is hydrogen, $C_1$-$C_8$alkyl or benzyl, and
n is 1 or 2
can be prepared by oxidation of the compounds of formula Ia.

For example, the compounds of formula Ib, wherein n is 1 can be prepared by oxidation of the compound of formula Ia with sodium periodate. For example, the compounds of formula Ib, wherein n is 2 can be prepared by oxidation of the compound of formula Ia with 3-chloroperoxybenzoic acid (m-CPBA).

The present invention relates therefore also to compounds of the formula II

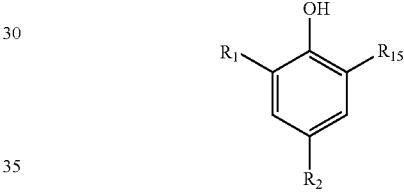
(II)

wherein
$R_1$ and $R_2$ independently of each other are hydrogen, $C_1$-$C_{25}$alkyl, $C_2$-$C_{25}$alkenyl, unsubstituted or with $C_1$-$C_4$alkyl substituted phenyl; unsubstituted or with $C_1$-$C_4$alkyl substituted $C_7$-$C_9$phenylalkyl; —CH($R_7$)—S(O)$_n$—CH$_2$—CH($R_7$)—$R_9$,
$R_7$ is hydrogen, $C_1$-$C_{12}$alkyl,

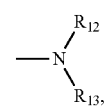

unsubstituted or with halogen or $C_1$-$C_4$alkyl substituted phenyl;
$R_9$ is —CN, —S(O)$_n$—$R_{10}$,

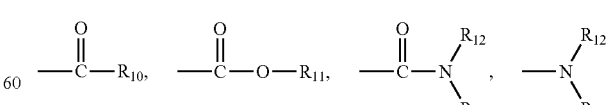

or —NO$_2$,
$R_{10}$ is hydrogen, $C_1$-$C_{25}$alkyl, $C_7$-$C_9$phenylalkyl, unsubstituted or $C_1$-$C_4$alkyl-substituted phenyl; unsubstituted or $C_1$-$C_4$alkyl-substituted $C_5$-$C_8$cycloalkyl;

R$_{11}$ is hydrogen, alkali metal, C$_1$-C$_{25}$alkyl, C$_7$-C$_9$phenylalkyl, unsubstituted or C$_1$-C$_4$alkyl-substituted phenyl; unsubstituted or C$_1$-C$_4$alkyl-substituted C$_5$-C$_8$cycloalkyl; or C$_3$-C$_{25}$alkyl which is interrupted by oxygen or sulfur;

R$_{12}$ and R$_{13}$ independently of one another are hydrogen, C$_1$-C$_{25}$alkyl, C$_1$-C$_4$alkanoyl, C$_7$-C$_9$-phenylalkyl, unsubstituted or C$_1$-C$_4$alkyl-substituted phenyl; or R$_{12}$ and R$_{13}$, together with the nitrogen atom to which they are attached, form a 5-, 6- or 7-membered heterocyclic ring which is unsubstituted or is substituted by C$_1$-C$_4$alkyl or is interrupted by oxygen, sulfur or

R$_{14}$ is hydrogen, C$_1$-C$_8$alkyl or benzyl,
R$_{15}$ is —CH(R$_7$)—S(O)$_n$—CH$_2$—CH(R$_7$)—R$_9$, and
n is 0 1 or 2.

The preferred general symbols are identical to those of the compounds of the formula I disclosed in the composition with an organic material. In addition, for the compounds of formula II n is preferably 0.

The phenols of the formula II are prepared according to conventional synthetic methods, for example compounds of formula II wherein n is 0 and R$_{7a}$ is H can be prepared by reacting the compound of formula IV

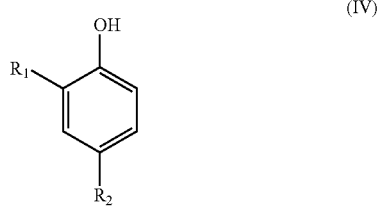

wherein R$_1$ and R$_2$ have the meaning as indicated for the compounds of formula II, with H—S(O)$_n$—CH$_2$—CH(R$_{7b}$)—R$_9$, wherein n is 0 and R$_{7b}$ and R$_9$ have the meaning as indicated for the compound of formula II, and paraformaldehyde.

A preferred embodiment of the present invention is also a process for stabilizing an organic material against oxidative, thermal or light-induced degradation and/or for reducing the surface energy of organic materials, which comprises incorporating therein or applying thereto at least a compound of the formula I.

Also a preferred embodiment of the present invention is the use of the compounds of the formula I as stabilizers against oxidative, thermal or light-induced degradation and/or as reducers of surface energy for organic materials.

The preferred compounds of the formula I for the process and use are the same as those described for the compositions with an organic material.

The compositions according to the invention can be advantageously used for the preparation of various shaped articles. Examples are:

I-1) Floating devices, marine applications, pontoons, buoys, plastic lumber for decks, piers, boats, kayaks, oars, and beach reinforcements.

I-2) Automotive applications, in particular bumpers, dashboards, battery, rear and front linings, moldings parts under the hood, hat shelf, trunk linings, interior linings, air bag covers, electronic moldings for fittings (lights), panes for dashboards, headlamp glass, instrument panel, exterior linings, upholstery, automotive lights, head lights, parking lights, rear lights, stop lights, interior and exterior trims; door panels; gas tank; glazing front side; rear windows; seat backing, exterior panels, wire insulation, profile extrusion for sealing, cladding, pillar covers, chassis parts, exhaust systems, fuel filter/filler, fuel pumps, fuel tank, body side mouldings, convertible tops, exterior mirrors, exterior trim, fasteners/fixings, front end module, glass, hinges, lock systems, luggage/roof racks, pressed/stamped parts, seals, side impact protection, sound deadener/insulator and sunroof.

I-3) Road traffic devices, in particular sign postings, posts for road marking, car accessories, warning triangles, medical cases, helmets, tires.

I-4) Devices for plane, railway, motor car (car, motorbike, trucks) including furnishings.

I-5) Devices for space applications, in particular rockets and satellites, e.g. reentry shields.

I-6) Devices for architecture and design, mining applications, acoustic quietized systems, street refuges, and shelters.

II-1) Appliances, cases and coverings in general and electric/electronic devices (personal computer, telephone, portable phone, printer, television-sets, audio and video devices), flower pots, satellite TV bowl, and panel devices.

II-2) Jacketing for other materials such as steel or textiles.

II-3) Devices for the electronic industry, in particular insulation for plugs, especially computer plugs, cases for electric and electronic parts, printed boards, and materials for electronic data storage such as chips, check cards or credit cards.

II-4) Electric appliances, in particular washing machines, tumblers, ovens (microwave oven), dish-washers, mixers, and irons.

II-5) Covers for lights (e.g. street-lights, lamp-shades).

II-6) Applications in wire and cable (semi-conductor, insulation and cable-jacketing).

II-7) Foils for condensers, refrigerators, heating devices, air conditioners, encapsulating of electronics, semi-conductors, coffee machines, and vacuum cleaners.

III-1) Technical articles such as cogwheel (gear), slide fittings, spacers, screws, bolts, handles, and knobs.

III-2) Rotor blades, ventilators and windmill vanes, solar devices, swimming pools, swimming pool covers, pool liners, pond liners, closets, wardrobes, dividing walls, slat walls, folding walls, roofs, shutters (e.g. roller shutters), fittings, connections between pipes, sleeves, and conveyor belts.

III-3) Sanitary articles, in particular shower cubicles, lavatory seats, covers, and sinks.

III-4) Hygienic articles, in particular diapers (babies, adult incontinence), feminine hygiene articles, shower curtains, brushes, mats, tubs, mobile toilets, tooth brushes, and bed pans.

III-5) Pipes (cross-linked or not) for water, waste water and chemicals, pipes for wire and cable protection, pipes for gas, oil and sewage, guttering, down pipes, and drainage systems.

III-6) Profiles of any geometry (window panes) and siding.

III-7) Glass substitutes, in particular extruded or co-extruded plates, glazing for buildings (monolithic, twin or multiwall), aircraft, schools, extruded sheets, window film for architectural glazing, train, transportation, sanitary articles, and greenhouse.

III-8) Plates (walls, cutting board), extrusion-coating (photographic paper, tetrapack and pipe coating), silos, wood substitute, plastic lumber, wood composites, walls, surfaces, furniture, decorative foil, floor coverings (interior and exterior applications), flooring, duck boards, and tiles.

III-9) Intake and outlet manifolds.

III-10) Cement-, concrete-, composite-applications and covers, siding and cladding, hand rails, banisters, kitchen work tops, roofing, roofing sheets, tiles, and tarpaulins.

IV-1) Plates (walls and cutting board), trays, artificial grass, astroturf, artificial covering for stadium rings (athletics), artificial floor for stadium rings (athletics), and tapes.

IV-2) Woven fabrics continuous and staple, fibers (carpets/hygienic articles/geotextiles/monofilaments; filters; wipes/curtains (shades)/medical applications), bulk fibers (applications such as gown/protection clothes), nets, ropes, cables, strings, cords, threads, safety seat-belts, clothes, underwear, gloves; boots; rubber boots, intimate apparel, garments, swimwear, sportswear, umbrellas (parasol, sunshade), parachutes, paraglides, sails, "balloon-silk", camping articles, tents, airbeds, sun beds, bulk bags, and bags. Non-woven fabrics such as medical fabrics and related apparel, industrial apparel, outdoor fabrics, in-home furnishing and construction fabrics.

IV-3) Membranes, insulation, covers and seals for roofs, tunnels, dumps, ponds, dumps, walls roofing membranes, geomembranes, swimming pools, curtains (shades)/sunshields, awnings, canopies, wallpaper, food packing and wrapping (flexible and solid), medical packaging (flexible & solid), airbags/safety belts, arm- and head rests, carpets, centre console, dashboard, cockpits, door, overhead console module, door trim, headliners, interior lighting, interior mirrors, parcel shelf, rear luggage cover, seats, steering column, steering wheel, textiles, and trunk trim.

V) Films (packaging, dump, laminating, agriculture and horticulture, greenhouse, mulch, tunnel, silage), bale wrap, swimming pools, waste bags, wallpaper, stretch film, raffia, desalination film, batteries, and connectors.

VI-1) Food packing and wrapping (flexible and solid), bottles.

VI-2) Storage systems such as boxes (crates), luggage, chest, household boxes, pallets, shelves, tracks, screw boxes, packs, and cans.

VI-3) Cartridges, syringes, medical applications, containers for any transportation, waste baskets and waste bins, waste bags, bins, dust bins, bin liners, wheely bins, container in general, tanks for water/used water/chemistry/gas/oil/gasoline/diesel; tank liners, boxes, crates, battery cases, troughs, medical devices such as piston, ophthalmic applications, diagnostic devices, and packing for pharmaceuticals blister.

VII-1) Extrusion coating (photo paper, tetrapack, pipe coating), household articles of any kind (e.g. appliances, thermos bottle/clothes hanger), fastening systems such as plugs, wire and cable clamps, zippers, closures, locks, and snap-closures.

VII-2) Support devices, articles for the leisure time such as sports and fitness devices, gymnastics mats, ski-boots, inline-skates, skis, big foot, athletic surfaces (e.g. tennis grounds); screw tops, tops and stoppers for bottles, and cans.

VII-3) Furniture in general, foamed articles (cushions, impact absorbers), foams, sponges, dish clothes, mats, garden chairs, stadium seats, tables, couches, toys, building kits (boards/figures/balls), playhouses, slides, and play vehicles.

VII-4) Materials for optical and magnetic data storage.

VII-5) Kitchen ware (eating, drinking, cooking, storing).

VII-6) Boxes for CD's, cassettes and video tapes; DVD electronic articles, office supplies of any kind (ball-point pens, stamps and ink-pads, mouse, shelves, tracks), bottles of any volume and content (drinks, detergents, cosmetics including perfumes), and adhesive tapes.

VII-7) Footwear (shoes/shoe-soles), insoles, spats, adhesives, structural adhesives, food boxes (fruit, vegetables, meat, fish), synthetic paper, labels for bottles, couches, artificial joints (human), printing plates (flexographic), printed circuit boards, and display technologies.

VII-8) Devices of filled polymers (talc, chalk, china clay (kaolin), wollastonite, pigments, carbon black, $TiO_2$, mica, nanocomposites, dolomite, silicates, glass, asbestos).

Thus, a further embodiment of the present invention relates to a shaped article, in particular a film, pipe, profile, bottle, tank or container, fiber containing a composition as described above.

A further embodiment of the present invention relates to a molded article containing a composition as described above. The molding is in particular effected by injection, blow, compression, roto-molding or slush-molding or extrusion.

As already mentioned, the organic materials to be protected are preferably organic, especially synthetic, polymers. In this context, thermoplastic materials are protected with particular advantage. Attention should be drawn above all in this context to the outstanding activity of the stabilizers of the formula I as processing stabilizers (heat stabilizers). For this purpose they are advantageously added to the polymer prior to or during its processing. However, other polymers too (for example elastomers) or lubricants or hydraulic fluids can be stabilized against degradation, for example light-induced or thermooxidative degradation. Elastomers can be taken from the above listing of possible organic materials.

The invention relates also to compositions comprising a functional fluid, preferably from the series of lubricants, hydraulic fluids and metal-working fluids and also fuels for powering engines of the 4-stroke, Otto, 2-stroke, diesel, Wankel and orbital types, and at least one compound of the formula I.

The compounds of the formula I may preferably be used in lubricants and fuels as multifunctional stabilizers, that is to say they combine in themselves antioxidative, friction-reducing, extreme-pressure-protection and wear-protection action and also anti-corrosion properties.

Preferred lubricants and fuels and related products are engine oils, turbine oils, gear oils, hydraulic fluids, diesel or Otto fuels, metal-working fluids and lubricating greases.

Especially preferred lubricants are mineral oils, synthetic oils or mixtures thereof.

Products known per se are used as functional fluids from the series of lubricants, hydraulic fluids and metal-working fluids.

The lubricants and hydraulic fluids that come into consideration will be familiar to the person skilled in the art and are described in the relevant specialist literature, such as, for example, in Dieter Klamann, "Schmierstoffe and verwandte Produkte" [Lubricants and related products] (Verlag Chemie, Weinheim, 1982), in Schewe-Kobek, "Das Schmiermittel-Taschenbuch" [The lubricant handbook] (Dr. Alfred Hüthig-Verlag, Heidelberg, 1974) and in "Ullmanns Enzyklopädie der technischen Chemie" [Ullmann's Encyclopaedia of Industrial Chemistry], Vol. 13, pages 85-94 (Verlag Chemie, Weinheim, 1977).

The lubricants are especially oils and greases, for example based on a mineral oil. Oils are preferred.

A further group of lubricants that may be used are vegetable or animal oils, greases, tallows and waxes or mixtures thereof with one another or mixtures with the mentioned mineral or synthetic oils.

Vegetable and animal oils, greases, tallows and waxes are, for example, palm-kernel oil, palm oil, olive oil, rapeseed oil, rape oil, linseed oil, groundnut oil, soybean oil, cottonseed oil, sunflower oil, pumpkin seed oil, coconut oil, maize oil, castor oil, tree nut oil and mixtures thereof, fish oils, tallows obtained from slaughtered animals, such as beef tallow, neatsfoot oil and bone oil, and modified, epoxidised and sulfoxidised forms thereof, for example epoxidised soybean oil.

The mineral oils are based especially on hydrocarbon compounds.

Examples of synthetic lubricants include lubricants based on aliphatic or aromatic carboxy esters, polymeric esters, polyalkylene oxides, phosphoric acid esters, poly-alpha-olefins or silicones, a diester of a divalent acid with a monohydric alcohol, such as, for example, dioctyl sebacate or dinonyl adipate, a triester of trimethylolpropane with a monovalent acid or with a mixture of such acids, such as, for example, trimethylolpropane tripelargonate, trimethylolpropane tricaprylate or mixtures thereof, a tetraester of pentaerythritol with a monovalent acid or with a mixture of such acids, such as, for example, pentaerythritol tetracaprylate, or a complex ester of monovalent and divalent acids with polyhydric alcohols, for example a complex ester of trimethylolpropane with caprylic and sebacic acid, or a mixture thereof. Apart from mineral oils there are especially suitable, for example, poly-alpha-olefins, ester-based lubricants, phosphates, glycols, polyglycols and polyalkylene glycols, and also mixtures thereof with water.

Metal-working fluids and hydraulic fluids may be prepared on the basis of the same substances as those described above for the lubricants, such fluids frequently being emulsions of such substances in water or other liquids.

Lubricant and fuel compositions according to the invention are used, for example, in internal combustion engines, e.g. in motorised vehicles equipped with, for example, engines of the Otto, diesel, two-stroke, Wankel or orbital type.

The compounds of the formula I are readily soluble in lubricants and fuels, metal-working fluids and hydraulic fluids and are therefore especially suitable as additives for lubricants and fuels, metal-working fluids and hydraulic fluids.

As additives in lubricants, the compounds of the formula I are effective even in very small amounts. They are mixed in with the lubricants advantageously in an amount of from 0.01 to 5% by weight, preferably in an amount of from 0.05 to 3% by weight and very especially in an amount of from 0.1 to 2% by weight, in each case based on the lubricant.

The compounds of the formula I may be mixed in with the lubricants and fuels in a manner known per se. The compounds of the formula I are readily soluble, for example, in oils. It is also possible to prepare a so-called master batch, which may be diluted, as a function of use, with the appropriate lubricant or fuel to the concentrations suitable for use. In such cases concentrations above 1% by weight are possible.

The lubricants and fuels, metal-working fluids and hydraulic fluids may additionally comprise other additives that are added in order to improve their basic properties still further; such additives include: further antioxidants, metal passivators, rust inhibitors, viscosity index improvers, pour-point depressants, dispersants, detergents, coefficient of friction reducers, further extreme-pressure additives and anti-wear additives. Such further additives are added advantageously in an amount of from 0.01 to 5% by weight.

A number of such compounds can be found, for example, in the above list "1. Antioxidants", especially points 1.1 to 1.19. In addition, further additives may be mentioned by way of example:

Examples of Further Antioxidants:
Aliphatic or aromatic phosphites, esters of thiodipropionic acid or thiodiacetic acid or salts of dithiocarbamic or dithiophosphoric acid, 2,2,12,12-tetramethyl-5,9-dihydroxy-3,7,11-trithiamidecane and 2,2,15,15-tetramethyl-5,12-dihydroxy-3,7,10,14-tetrathiahexadecane.

Examples of Metal Deactivators, e.g. for Copper, are:
a) Benzotriazoles and derivatives thereof, e.g. 2-mercaptobenzotriazole, 2,5-dimercaptobenzotriazole, 4- or 5-alkylbenzotriazoles (e.g. tolutriazole) and derivatives thereof, 4,5,6,7-tetrahydrobenzotriazole, 5,5'-methylenebis-benzotriazole; Mannich bases of benzotriazole or tolutriazole, such as 1-[di(2-ethylhexyl)aminomethyl]tolutriazole and 1-[di(2-ethylhexyl)aminomethyl]benzotriazole; alkoxyalkylbenzotriazoles, such as 1-(nonyloxymethyl)benzotriazole, 1-(1-butoxyethyl)benzotriazole and 1-(1-cyclohexyloxybutyl)tolutriazole.
b) 1,2,4-Triazoles and derivatives thereof, e.g. 3-alkyl-(or -aryl-)1,2,4-triazoles, Mannich bases of 1,2,4-triazoles, such as 1-[di(2-ethylhexyl)aminomethyl]-1,2,4-triazole; alkoxyalkyl-1,2,4-triazoles, such as 1-(1-butoxyethyl)-1,2,4-triazole; acylated 3-amino-1,2,4-triazoles.
c) Imidazole derivatives, e.g. 4,4'-methylenebis(2-undecyl-5-methyl)imidazole and bis[(N-methyl)imidazol-2-yl] carbinol-octyl ether.
d) Sulfur-containing heterocyclic compounds, e.g. 2-mercaptobenzothiazole, 2,5-dimercapto-1,3,4-thiadiazole, 2,5-dimercaptobenzothiadiazole and derivatives thereof; 3,5-bis[di(2-ethylhexyl)aminomethyl]-1,3,4-thiadiazolin-2-one.
e) Amino compounds, e.g. salicylidene-propylenediamine, salicylaminoguanidine and salts thereof.

Examples of Rust Inhibitors are:
a) Organic acids, their esters, metal salts, amine salts and anhydrides, e.g. alkyl- and alkenyl-succinic acids and their partial esters with alcohols, diols or hydroxycarboxylic acids, partial amides of alkyl- and alkenyl-succinic acids, 4-nonylphenoxyacetic acid, alkoxy- and alkoxyethoxycarboxylic acids, such as dodecyloxyacetic acid, dodecyloxy(ethoxy)acetic acid and amine salts thereof, and also N-oleoyl-sarcosine, sorbitan monooleate, lead naphthenate, alkenylsuccinic acid anhydrides, e.g. dodecenylsuccinic acid anhydride, 2-(2-carboxyethyl)-1-dodecyl-3-methylglycerol and salts thereof, especially sodium and triethanolamine salts thereof.
b) Nitrogen-containing compounds, e.g.:
   i. Primary, secondary or tertiary, aliphatic or cycloaliphatic amines and amine salts of organic and inorganic acids, e.g. oil-soluble alkylammonium carboxylates, and 1-[N,N-bis(2-hydroxyethyl)amino]-3-(4-nonylphenoxy)propan-2-ol.
   ii. Heterocyclic compounds, e.g.: substituted imidazolines and oxazolines, e.g. 2-heptadecenyl-1-(2-hydroxyethyl)-imidazoline.
c) Phosphorus-containing compounds, e.g.:
   Amine salts of phosphoric acid partial esters or phosphonic acid partial esters, zinc dialkyldithiophosphates.
d) Sulfur-containing compounds, e.g.:
   Barium dinonylnaphthalene sulfonates, calcium petroleum sulfonates, alkylthio-substituted aliphatic carboxylic acids, esters of aliphatic 2-sulfocarboxylic acids and salts thereof.
e) Glycerol derivatives, e.g.:
   Glycerol monooleate, 1-(alkylphenoxy)-3-(2-hydroxyethyl)glycerols, 1-(alkylphenoxy)-3-(2,3-dihydroxypropyl)glycerols, 2-carboxyalkyl-1,3-dialkylglycerols.

Examples of Viscosity Index Improvers are:
Polyacrylates, polymethacrylates, vinylpyrrolidone/methacrylate copolymers, polyvinylpyrrolidones, polybutenes, olefin copolymers, styrene/acrylate copolymers, polyethers.

Examples of Pour-Point Depressants are:
Poly(meth)acrylates, ethylene/vinyl acetate copolymer, alkylpolystyrenes, fumarate copolymers, alkylated naphthalene derivatives.

Examples of Dispersants/Surfactants are:
Polybutenylsuccinic acid amides or imides, polybutenylphosphonic acid derivatives, basic magnesium, calcium and barium sulfonates and phenolates.

Examples of Extreme-Pressure and Anti-Wear Additives are:
Sulfur- and/or phosphorus- and/or halogen-containing compounds, such as, for example, chlorinated paraffins, sulfurated olefins or vegetable oils (soybean/rape oil), alkyl- or aryl-di- or -tri-sulfides, zinc dialkyldithiophosphates, zinc dithiocarbamates such as zinc diamyldithiocarbamate, molybdenum dithioates such as molybdenum dithiocarbamates, friaryl phosphates such as tritolyl phosphate, tricresyl phosphate, phenyl phosphate isopropyl ester, amine salts of mono- or di-alkylphosphoric acids such as the amine salts of mono-/di-hexyl phosphate, amine salts of alkylphosphonic acids such as the amine salt of methylphosphonic acid, triaryl phosphites such as tris[nonylphenyl]phosphite, dialkyl phosphites such as dioctyl phosphite, triaryl monothiophosphates such as triphenyl thionophosphate or tris[iso-nonylphenyl] thionophosphate or tert-butylated triphenyl thionophosphate, substituted trialkyl mono- or di-thiophosphates such as diisopropoxyphosphinothioyl)thio]propionate or butylene-1,3-bis [(diisobutoxyphosphinothioyl)propionate, trithiophosphates such as trithiophosphoric acid S,S,S-tris(isooctyl-2-acetates), amine salts of 3-hydroxy-1,3-thiaphosphetane-3-oxide, benzotriazoles or derivatives thereof such as bis(2-ethylhexyl)aminomethyl-tolutriazole, dithiocarbamates such as methylene-bis-dibutyldithiocarbamate, derivatives of 2-mercaptobenzothiazole such as 1-[N,N-bis(2-ethylhexyl)aminomethyl]-2-mercapto-1H-1,3-benzothiazole, derivatives of 2,5-dimercapto-1,3,4-thiadiazole such as 2,5-bis(tert-nonyldithio)-1,3,4-thiadiazole.

Examples of Coefficient of Friction Reducers are:
Lard oil, oleic acid, tallow, rape oil, sulfurated fats, amines. Further examples are given in EP-A-0 565 487.

Examples of Special Additives for Use in Water/Oil Metal-Working Fluids and Hydraulic Fluids are:
Emulsifiers: petroleum sulfonates, amines, such as polyoxyethylated fatty amines, non-ionic surface-active substances;
Buffers: alkanolamines;
Biocides: triazines, thiazolinones, tris-nitromethane, morpholine, sodium pyridenethol;
Speed improvers: calcium and barium sulfonates;

Examples of Fuel Additives:
Fuel additives are described in Kirk-Othmer, Encyclopedia of Chemical Technology, Vol 12, 1994 and in this instance are essentially petrol and diesel additives:
Petrol: dyes, especially azo dyes;
Antioxidants: aminic, especially para-phenylenediamines, or phenolic, e.g. 2,6-di-tert-butylphenol, as described above;
Metal deactivators: especially N,N'-disalicylidene-1,2-propane, benzotriazole, EDTA;
Rust inhibitors: for example carboxylic acids, sulfonates, amines or amine salts;
Dispersants: e.g. esters, high-molecular-weight amines, Mannich bases, succinimides, borated succinimides;
Detergents: for example fatty acid amides, nonpolymeric amines, polybutene succinimides, polyether amines, low-molecular-weight amines, sulfonates, salicylic acid derivatives;
Demulsifiers: for example long-chain alcohols or phenols containing poly-ethylene or -butylene groups;
Antiknock agents: tetralkyl lead, manganese methylcyclopentadienyltricarbonyl;
Oxygen compounds: esters of vegetable oils, ethers, alcohols for improving burn behaviour;
Diesel: ignition improvers (cetane improvers), e.g. alkyl nitrates, ether nitrates, alkyl diglycol nitrates, organic peroxides;
Stabilizers for, especially, cracked diesel: amines and other N-containing compounds that act as radical traps.

Especially preferred further additives in lubricants are aminic antioxidants, especially mixtures of mono- and di-alkylated tert-butyl-/tert-octyl-diphenylamines.

The present invention relates also to the use of the components of the formula I for stabilizing organic materials against oxidative, thermal or light-induced degradation, especially as additives in lubricants and fuels, hydraulic fluids or metal-working fluids, preferably in hydraulic oils and gear oils. The use according to the invention includes protection of the metal components to be lubricated against mechanical attrition (wear protection) and corrosion protection activity and also antioxidation activity—with respect both to the lubricant and to the metal components.

The examples which follow illustrate the invention in more detail. Parts and percentages are by weight.

EXAMPLE 1

Preparation of the Compound 101 (Table 1)

2.00 g (5.91 mmol) of 3-(3-tert-butyl-2-hydroxy-5-methyl-benzylsulfanyl)-propionic acid butyl ester [compound 201, Table 2] is dissolved in 22 ml of sulfolane to which 7.93 g (29.6 mmol) of diiodomethane is added at room temperature, followed by the addition of 0.59 g (14.8 mmol) of pulverized sodium hydroxide. The reaction is stirred at room temperature for 5 hours. Hexane is added and the organic phase is washed repeatedly with water, 1M $NH_4Cl$ and brine until neutral pH. The organic phase is dried over magnesium sulfate, filtered and concentrated using a vacuum rotary evaporator to give 6.0 g of a pale yellow liquid. The volatiles are distilled in a Kugelrohr (0.5 mbar; temperature: 80-95° C.) and then the residue is purified by flash chromatography (hexane/ethyl acetate: 40:1) to give 0.95 g of compound 101 as a white solid, m.p. 63-66° C. $^1H$ NMR: (300 MHz, $CDCl_3$): δ=7.01 (s, ArH, 1H); 6.76 (s, ArH, 1H); 5.27 (s, $OCH_2S$, 2H); 3.93 (s, $ArCH_2$, 2H); 2.28 (s, $CH_3$, 3H); 1.39 (s, tert-butyl, 9H). $^{13}C$ NMR (100 MHz, $CDCl_3$): 150.89 (s); 139.16 (s); 129.16 (s); 127.86 (d); 126.57 (d); 119.53 (s); 68.13 (t); 34.93 (s); 30.01 (q); 28.82 (t); 20.84 (q).

In analogy to Example 1 starting from the compounds 202, 203, 204, 205, 206 and 207 (see Table 2) the compounds 102, 103, 104, 105, 106 and 107 are prepared. In analogy to Example 1 starting from compound 210 (see Table 2) the compound 102 is prepared. In analogy to Example 1 starting from compound 211 (see Table 2) the compound 101 is prepared. In analogy to Example 1 starting from compound 212 (see Table 2) the compound 104 is prepared.

Compound 102: White solid; m.p. 50-51° C. $^1H$ NMR: (400 MHz, $CDCl_3$): δ=6.88 (s, ArH, 1H); 6.73 (s, ArH, 1H); 5.29 (s, $OCH_2S$, 2H); 3.89 (s, $ArCH_2$, 2H); 2.25 (s, $CH_3$, 3H); 2.18 (s, $CH_3$, 3H). $^{13}C$ NMR (100 MHz, $CDCl_3$): 149.86 (s); 130.38 (d); 129.21 (s); 127.45 (s); 127.19 (d); 118.65 (s); 68.89 (t); 28.71 (t); 20.33 (q); 16.02 (q).

Compound 103: Pale yellow solid; m.p. 103-104° C. $^1H$ NMR: (400 MHz, $CDCl_3$): δ=7.55-7.20 (m, ArH, 5H); 6.97 (s, ArH, 1H); 6.63 (s, ArH, 1H); 5.31 (d, J=11.2 Hz, OCHHS, 1H); 5.24 (s, ArCHAr, 1H); 5.12 (d, J=11.2 Hz; OCHHS, 1H);

2.28 (s, CH$_3$, 3H); 2.22 (s, CH$_3$, 3H). $^{13}$C NMR: (100 MHz, CDCl$_3$): δ=150.10 (s); 143.54 (s); 130.98 (d); 129.11 (s); 128.82 (d); 128.36 (d); 128.30 (d); 127.49 (s); 127.24 (d); 120.68 (s); 65.26 (t); 44.03 (d); 20.43 (q); 16.44 (q).

Compound 104: White solid; m.p. 122-124° C. $^1$H NMR: (300 MHz, CDCl$_3$): δ=7.30-7.10 (m, ArH, 6H); 6.70 (d, J=2.4 Hz, ArH, 1H); 5.20 (d, J=10.8 Hz, OCHHS, 1H); 5.18 (s, ArCHAr, 1H); 4.97 (d, J=10.8 Hz, OCHHS, 1H); 1.35 (s, tert-butyl, 9H); 1.14 (s, tert-butyl, 9H). $^{13}$C NMR: (100 MHz, CDCl$_3$): δ=150.77 (s); 143.92 (s); 141.99 (s); 138.39 (s); 128.79 (d); 128.28 (d); 127.09 (d); 125.36 (d); 123.46 (d); 120.56 (s); 64.53 (t); 44.54 (d); 35.33 (s); 34.24 (s); 31.47 (q); 30.06 (q).

Compound 105: Pale yellow liquid. $^1$H NMR: (300 MHz, CDCl$_3$): δ=6.97 (s, ArH, 1H); 6.81 (s, ArH, 1H); 5.27 (s, OCH$_2$S, 2H); 3.88 (s, ArCH$_2$S, 2H); 3.72 (s, ArCH$_2$S, 2H); 2.75-2.55 (m, SCH$_2$CH$_2$CF$_2$, 2H); 2.45-2.20 (m, CH$_2$CH$_2$CF$_2$, 2H); 2.26 (s, CH$_3$, 3H). $^{13}$C NMR: (100 MHz, CDCl$_3$): δ=149.38 (s); 130.04 (d); 129.73 (s); 129.12 (d); 127.11 (s); 119.53 (s); 69.02 (t); 31.98 (t, $^2$J(C, F)=22 Hz); 29.87 (t); 28.69 (t); 22.03 (t); 20.33 (q).

Compound 106: Colourless liquid. $^1$H NMR: (300 MHz, CDCl$_3$): δ=6.99 (s, ArH, 1H); 6.78 (s, ArH, 1H); 5.28 (s, OCH$_2$S, 2H); 4.20-4.05 (t, J=6.6 Hz, CO$_2$CH$_2$, 2H); 3.82 (s, ArCH$_2$S, 2H); 3.63 (s, ArCH$_2$S, 2H); 2.85-2.55 (m, SCH$_2$CH$_2$CO, 4H); 2.26 (s, ArCH$_3$, 3H); 1.80-1.55 (m, CO$_2$CH$_2$CH$_2$, 2H); 1.50-1.30 (m, CO$_2$CH$_2$CH$_2$CH$_2$, 2H); 0.95 (t, J=7.2 Hz, CH$_3$, 3H). $^{13}$C NMR (100 MHz, CDCl$_3$): 172.15 (s); 149.43 (s); 129.96 (d); 129.55 (s); 128.85 (d); 127.58 (s); 119.31 (s); 68.97 (t); 64.53 (t); 34.81 (t); 30.66 (t); 29.94 (t); 28.66 (t); 26.73 (t); 20.41 (q); 19.15 (t); 13.73 (q).

Compound 107: Colourless liquid. $^1$H NMR: (400 MHz, CDCl$_3$): δ=7.00 (s, ArH, 1H); 6.84 (s, ArH, 1H); 5.30 (s, OCH$_2$S, 2H); 3.89 (s, ArCH$_2$S, 2H); 3.66 (s, ArCH$_2$S, 2H); 2.70-2.60 (m, SCH$_2$CH$_2$CF$_2$, 2H); 2.45-2.15 (m, SCH$_2$CH$_2$CF$_2$, 2H); 2.19 (s, CH$_3$, 3H). $^{13}$C NMR: (100 MHz, CDCl$_3$): δ=151.32 (s); 130.02 (d); 128.71 (s); 128.25 (s); 127.20 (d); 119.10 (s); 69.01 (t); 35.86 (t); 31.77 (t, J=22 Hz); 28.75 (t); 21.94 (t); 16.10 (q).

EXAMPLE 2

Preparation of the Compound 108 (Table 1)

2.00 g (6.75 mmol) of 3-(2-hydroxy-3,5-dimethyl-benzylsulfanyl)-propionic acid butyl ester [compound 202, Table 2] and 5.43 g (33.8 mmol) of benzal chloride are dissolved in 25 ml of sulfolane to which 0.68 g (16.9 mmol) of pulverized sodium hydroxide is added at room temperature. The reaction is stirred at 60° C. for 3 hours. Hexane is added and the organic phase is washed repeatedly with water, 1M NH$_4$Cl and brine until neutral pH. The organic phase is dried over magnesium sulfate, filtered and concentrated using a vacuum rotary evaporator to give 6.70 g of an orange liquid. The volatiles are distilled in a Kugelrohr (0.3 mbar; temperature: 60-80° C.) and then the residue is purified by flash chromatography (hexane/ethyl acetate: 9:1) to give 0.35 g of the compound 108 as a white solid, m.p. 109-110° C. $^1$H NMR: (300 MHz, CDCl$_3$): δ=7.65-7.55 (m, ArH, 2H); 7.50-7.30 (m, ArH, 3H); 6.93 (s, ArH, 1H); 6.80 (s, ArH, 1H); 6.22 (s, OCHS, 1H); 4.16 (d, J=16 Hz, ArCHHS, 1H); 3.70 (d, J=16 Hz, ArCHHS, 1H); 2.28 (s, CH$_3$, 3H); 2.26 (s, CH$_3$, 3H). $^{13}$C NMR (100 MHz, CDCl$_3$): 150.58 (s); 138.57 (s); 130.40 (d); 129.43 (s); 128.64 (d); 128.53 (d); 127.70 (d); 126.93 (d); 126.25 (d); 118.36 (s); 81.60 (d); 30.09 (t); 20.44 (q); 16.25 (q).

In analogy to Example 2 starting from compound 206 (see Table 2) the compound 109 is prepared.

Compound 109: Pale yellow liquid. $^1$H NMR: (400 MHz, CDCl$_3$): δ=7.70-7.60 (m, ArH, 2H); 7.50-7.35 (m, ArH, 3H); 7.06 (s, ArH, 1H); 6.87 (s, ArH, 1H); 6.23 (s, OCHS, 1H); 4.33 (d, J=16 Hz, ArCHHSCHO; 1H); 4.11 (t, J=13 Hz, CO$_2$CH$_2$, 2H); 3.79 (t, J=13 Hz, ArCH$_2$S, 2H); 3.70 (d, J=16 Hz, ArCHHSCHO, 1H); 2.85-2.50 (m, SCH$_2$CH$_2$CO$_2$, 4H); 2.31 (s, ArCH$_3$, 3H); 1.70-1.55 (m, CO$_2$CH$_2$CH$_2$, 2H); 1.50-1.30 (m, CO$_2$CH$_2$CH$_2$CH$_2$, 2H); 0.96 (t, J=7.2 Hz, CH$_3$, 3H). $^{13}$C NMR (100 MHz, CDCl$_3$): 172.09 (s); 150.19 (s); 138.22 (s); 129.92 (d); 129.72 (s); 128.76 (d); 128.56 (d); 127.78 (s); 126.36 (d); 119.02 (s); 81.88 (d); 64.49 (t); 34.82 (t); 30.65 (t); 30.20 (t); 30.00 (t); 26.77 (t); 20.48 (q); 19.15 (t); 13.74 (q).

EXAMPLE 3

Preparation of the Compound 110 (Table 1)

3.84 g (8.40 mmol) of 3-[(3,5-di-tert-butyl-2-hydroxyphenyl)-phenyl-methylsulfanyl]-propionic acid butyl ester [compound 204, Table 2] and 6.76 g (42.0 mmol) of benzal chloride are dissolved in 47 ml of sulfolane to which 0.84 g (21.0 mmol) of pulverized sodium hydroxide is added at room temperature. The reaction is stirred at 55° C. for 15 hours. Hexane is added and the organic phase is washed repeatedly with water and brine until neutral pH. The organic phase is dried over magnesium sulfate, filtered and concentrated using a vacuum rotary evaporator to give 9.80 g of an orange liquid. The volatiles are distilled in a Kugelrohr (0.08 mbar; temperature: 120° C.) and then the residue is crystallized in acetonitrile to give 1.30 g of the compounds 110a and 110b as a mixture of diastereoisomers, pale yellow solid. Both diastereoisomers are subsequently separated via multiple crystallization to give the major diastereoisomer 110a as a pale yellow solid, m.p. 161-164° C. and the minor diastereoisomer 110b as a pale yellow solid, m.p. 120-125° C.

Major diastereoisomer (compound 110a): $^1$H NMR: (300 MHz, CDCl$_3$): δ=7.60-7.50 (m, ArH, 2H); 7.45-7.10 (m, ArH, 9H); 6.64 (d, J=2.4 Hz, ArH, 1H); 6.30 (s, OCHS, 1H); 5.69 (s, ArCHAr, 1H); 1.33 (s, tert-butyl, 9H); 1.07 (s, tert-butyl, 9H). $^{13}$C NMR: (100 MHz, CDCl$_3$): δ=152.24 (s); 142.47 (s); 141.28 (s); 138.79 (s); 137.93 (s); 129.13 (d); 128.76 (d); 128.60 (d); 128.58 (d); 127.67 (d); 126.53 (d); 124.38 (d); 123.45 (s); 122.91 (d); 82.79 (d); 48.93 (d); 35.33 (s); 34.31 (s); 31.35 (q); 30.20 (q).

Minor diastereoisomer (compound 110b): $^1$H NMR: (300 MHz, CDCl$_3$): δ=7.55-7.45 (m, ArH, 2H); 7.45-7.20 (m, ArH, 9H); 6.93 (d, J=2.4 Hz, ArH, 1H); 5.95 (s, OCHS, 1H); 5.30 (s, ArCHAr, 1H); 1.45 (s, tert-butyl, 9H); 1.29 (s, tert-butyl, 9H). $^{13}$C NMR: (100 MHz, CDCl$_3$): δ=151.68 (s); 145.21 (s); 142.36 (s); 138.72 (s); 138.03 (s); 128.61 (d); 128.58 (d); 128.42 (d); 128.27 (d); 126.91 (d); 126.72 (d); 125.49 (d); 123.56 (d); 119.55 (s); 77.49 (d); 46.45 (d); 35.38 (s); 34.28 (s); 31.50 (q); 30.17 (q).

EXAMPLE 4

Preparation of the Compound 111 (Table 1)

To a mixture of 5.97 g (5.46 mmol) of compound 208 [preparation see WO-A-2007/144283, Example 1] and 11.1 g (131 mmol) of dichloromethane are added at room temperature 16 ml of 1-methyl-2-pyrrolidinone (NMP) and 0.55 g (13.6 mmol) of pulverized sodium hydroxide. The reaction is stirred at 60° C. for 5 h. Ethyl acetate and tetrahydrofuran are added and the organic phase is washed repeatedly with water and brine until neutral pH. The organic phase is dried over magnesium sulfate, filtered and concentrated using a vacuum rotary evaporator. The brown residue oil is purified by flash chromatography (hexane) to give 0.30 g of the compound 111 as a white solid, m.p. 68-69° C. $^1$H NMR: (400 MHz, CDCl$_3$): δ=6.98 (s, ArH, 1H); 6.81 (s, ArH, 1H); 5.27 (s, OCH$_2$S, 2H); 3.88 (s, ArCH$_2$S, 2H); 3.72 (s, ArCH$_2$S, 2H); 2.75-2.65 (m, SCH$_2$CH$_2$CF$_2$, 2H); 2.50-2.25 (m, SCH$_2$CH$_2$CF$_2$, 2H); 2.26 (s, CH$_3$, 3H). $^{13}$C NMR (75 MHz, CDCl$_3$): 149.78 (s); 130.42 (d); 130.11 (s); 129.49 (d); 127.51 (s); 119.93 (s); 69.40 (t); 32.51 (t, $^2$J(C, F)=22 Hz); 30.28 (t); 29.07 (t); 22.47 (t); 20.68 (q).

In analogy to Example 4 starting from compound 209 (see Table 2) the compound 112 is prepared.

Compound 112: White solid; m.p. 68-69° C. $^1$H NMR: (300 MHz, CDCl$_3$): δ=6.99 (s, ArH, 1H); 6.84 (s, ArH, 1H); 5.30 (s, OCH$_2$S, 2H); 3.89 (s, ArCH$_2$S, 2H); 3.66 (s, ArCH$_2$S, 2H); 2.75-2.55 (m, SCH$_2$CH$_2$CF$_2$, 2H); 2.45-2.10 (m, SCH$_2$CH$_2$CF$_2$, 2H); 2.19 (s, CH$_3$, 3H). $^{13}$C NMR (75 MHz, CDCl$_3$): 151.70 (s); 130.40 (d); 129.09 (s); 128.62 (s); 127.59 (d); 119.58 (s); 69.37 (t); 36.20 (t); 32.21 (t, $^2$J(C, F)=22 Hz); 29.11 (t); 22.32 (t); 16.45 (q).

EXAMPLE 5

Preparation of the Compound 113 (Table 1)

0.87 g (1.55 mmol) of a 10% aqueous solution of potassium carbonate is added dropwise at room temperature to a mixture of 0.35 g (1.03 mmol) of 3-(6-methyl-4H-1-oxa-3-thia-naphthalen-8-ylmethylsulfanyl)-propionic acid butyl ester [compound 106, Table 1, Example 1] and 2 ml of methanol. The reaction is stirred at room temperature for 5 hours, then 1M HCl is added until pH is 1. Ethyl acetate is added and the organic phase is washed repeatedly with water and brine until neutral pH. The organic phase is dried over magnesium sulfate, filtered and concentrated using a vacuum rotary evaporator to give a crude material which is purified by flash chromatography (hexane/ethyl acetate: 1:1) to give 0.17 g of the compound 113 as a white solid, m.p. 86-88° C. $^1$H NMR: (400 MHz, CDCl3): δ=7.00 (s, ArH, 1H); 6.80 (s, ArH, 1H); 5.29 (s, OCH2S, 2H); 3.89 (s, ArCH2S, 2H); 3.72 (s, ArCH2S, 2H); 2.85-2.60 (m, SCH2CH2CO2, 4H); 2.27 (s, CH3, 3H). $^{13}$C NMR (100 MHz, CDCl$_3$): 177.95 (s); 149.43 (s); 129.98 (d); 129.63 (s); 128.94 (d); 127.40 (s); 119.37 (s); 69.01 (t); 34.54 (t); 29.95 (t); 28.67 (t); 26.27 (t); 20.41 (q).

EXAMPLE 6

Preparation of the Compound 114 (Table 1)

1.19 g (5.55 mmol) of sodium periodate in 5 ml of water is added dropwise at 0-5° C. to a solution of 1.00 g (5.55 mmol) of 6,8-dimethyl-4H-1-oxa-3-thia-naphthalene [compound 102, Table 1, Example 1] in 15 ml of methanol. The reaction is stirred at 0° C. for 30 minutes and at room temperature for 12 hours. Dichloromethane is added and the white solid is filtered off. The filtrate is concentrated using a vacuum rotary evaporator and the residue is dissolved in dichloromethane. The organic phase is washed repeatedly with water and brine, dried over magnesium sulfate, filtered and concentrated using a vacuum rotary evaporator to give a crude material which is purified by flash chromatography (dichloromethane/methanol: 19:1) to give 0.23 g of the compound 114 as a white solid, m.p. 215-220° C. $^1$H NMR: (300 MHz, CDCl$_3$): δ=6.95 (s, ArH, 1H); 6.77 (s, ArH, 1H); 4.96 (s, OCH$_2$SO, 2H); 4.11 (d, J=15.6 Hz, ArCHHSO, 1H); 3.98 (d, J=15.6 Hz, ArCHHSO, 1H); 2.27 (s, CH$_3$, 3H); 2.24 (s, CH$_3$, 3H). $^{13}$C NMR: (100 MHz, CDCl$_3$): δ=148.76 (s); 132.11 (s); 131.71 (d); 129.02 (d); 127.10 (s); 113.01 (s); 80.12 (t); 49.32 (t); 20.47 (q); 15.85 (q).

In analogy to Example 6 starting from compound 104 (see Table 1) the compounds 115a and 115b as a mixture of diastereoisomers, white solid, are prepared. Both diastereoisomers are subsequently separated via preparative HPLC (normal phase, solvent gradient: 15% ethylacetate/85% heptane to 100% ethylacetate) to give the major diastereoisomer 115a as a white solid, m.p. 184-186° C. and the minor diastereoisomer 115b as a white solid, m.p. 172-174° C.

Major diastereoisomer (compound 115a): $^1$H NMR: (400 MHz, CDCl$_3$): δ=7.50-7.20 (m, ArH, 6H); 6.88 (s, ArH, 1H); 5.30 (s, ArCHAr, 1H); 5.00 (d; J=11.2 Hz, OCHHSO, 1H); 4.79 (d, J=11.2 Hz, OCHHSO, 1H); 1.47 (s, tert-butyl, 9H); 1.25 (s, tert-butyl, 9H). $^{13}$C NMR: (100 MHz, CDCl$_3$): δ=149.75 (s); 145.05 (s); 138.33 (s); 135.34 (s); 129.76 (d); 129.22 (d); 128.55 (d); 126.77 (d); 124.57 (d); 116.48 (s); 75.43 (t); 65.34 (d); 35.16 (s); 34.47 (s); 31.41 (q); 30.02 (q).

Minor diastereoisomer (compound 115b): $^1$H NMR: (400 MHz, CDCl$_3$): δ=7.55-7.20 (m, ArH, 6H); 6.88 (s, ArH, 1H); 5.21 (d, J=10.4 Hz, OCHHSO, 1H); 5.16 (s, ArCHAr, 1H); 4.66 (d, J=10.4 Hz, OCHHSO, 1H); 1.45 (s, tert-butyl, 9H); 1.22 (s, tert-butyl, 9H). $^{13}$C NMR: (100 MHz, CDCl$_3$): δ=150.56 (s); 145.30 (s); 138.47 (s); 132.49 (s); 130.82 (d); 128.77 (d); 128.54 (d); 126.04 (d); 124.54 (d); 119.12 (s); 79.48 (t); 62.22 (d); 35.08 (s); 34.52 (s); 31.37 (q); 30.07 (q).

EXAMPLE 7

Preparation of the Compound 116 (Table 1)

0.25 g (1.02 mmol) of 3-chloroperoxybenzoic acid (m-CPBA) in 5 ml of dichloromethane is added at 0° C. to a solution of 0.20 g (1.02 mmol) of 6,8-dimethyl-4H-1-oxa-3-thia-naphthalene 3-oxide [compound 114, Table 1, Example 6] in 20 ml of dichloromethane. The reaction is stirred at 0° C. for 3 hours. Ethyl acetate is added and the organic phase is washed repeatedly with aqueous sodium sulfite, water and brine. The organic phase is dried over magnesium sulfate, filtered and concentrated using a vacuum rotary evaporator to give a crude material which is purified by flash chromatography (dichloromethane/methanol: 19:1) to give 0.15 g of the compound 116 as a white solid, m.p. 115-117° C. $^1$H NMR: (400 MHz, CDCl$_3$): δ=7.00 (s, ArH, 1H); 6.74 (s, ArH, 1H); 4.89 (s, OCH$_2$SO$_2$, 2H); 4.34 (s, ArCH$_2$SO$_2$, 2H); 2.29 (s, CH$_3$, 3H); 2.26 (s, CH$_3$, 3H). $^{13}$C NMR: (100 MHz, CDCl$_3$): δ=148.83 (s); 133.84 (s); 132.17 (s); 128.34 (s); 128.18 (d); 116.35 (s); 81.25 (t); 53.06 (t); 20.48 (q); 15.88 (q).

EXAMPLE 8

Preparation of the Compound 117 (Table 1)

To a solution of 2.50 g (10.5 mmol) of the compound 120 [Example 11, Table 1] in 80 ml of dichloromethane is added a dried MgSO$_4$ solution of 2.17 g (12.6 mmol) of 3-chloroperoxybenzoic acid (m-CPBA) in 20 ml of dichloromethane at 0-5° C. The reaction is stirred at room temperature for 3 h. Water is then added and the organic phase is washed with an aqueous solution of sodium sulfite and water. The organic phase is dried over magnesium sulfate, filtered and concentrated using a vacuum rotary evaporator to give 3.10 g of a colourless liquid. The crude product is purified by flash chromatography (dichloromethane/methanol: 19:1) to give 2.50 g of the compound 117 as white solid, m.p. 113-114° C. $^1$H NMR: (400 MHz, CDCl$_3$): δ=7.15 (s, ArH, 1H); 6.89 (s, ArH, 1H); 4.85 (s, OCH$_2$SO$_2$, 2H); 4.30 (s, ArCH$_2$SO$_2$, 2H); 2.33 (s, CH$_3$, 3H); 1.38 (s, tert-butyl, 9H). $^{13}$C NMR: (100 MHz, CDCl$_3$): δ=151.65 (s); 140.78 (s); 134.80 (s); 128.68 (d); 128.55 (d); 120.50 (s); 83.91 (t); 53.62 (t); 34.55 (s); 30.00 (q); 21.01 (q).

EXAMPLE 9

Preparation of the Compound 118 (Table 1)

5.28 g (24.7 mmol) of sodium periodate in 50 ml of water is added dropwise at 50° C. to a suspension of 4.00 g (15.6 mmol) of 6,8-dimethyl-4-phenyl-4H-1-oxa-3-thia-naphthalene [compound 103, Table 1, Example 1] in 120 ml of isopropanol. The reaction is stirred at 70° C. for 18 hours. Dichloromethane is added and the organic phase is washed repeatedly with water and brine, dried over magnesium sulfate, filtered and concentrated using a vacuum rotary evaporator to give a crude material which is purified by crystallization in ethyl acetate to give 2.10 g of the compound 118 as a white solid, m.p. 226-229° C. $^1$H NMR: (300 MHz, CDCl$_3$): δ=7.45-7.30 (m, ArH, 3H); 7.25-7.15 (m, ArH, 2H); 7.04 (s, ArH, 1H); 6.71 (s; ArH; 1H); 5.31 (s; ArCHAr; 1H); 5.04 (d, J=11.1 Hz; OCHHSO; 1H); 4.66 (d, J=11.1 Hz, OCHHSO; 1H); 2.34 (s; CH$_3$, 3H); 2.24 (s; CH$_3$, 3H). $^{13}$C NMR: (100 MHz, CDCl$_3$): δ=148.30 (s); 135.77 (s); 132.14 (d); 131.72 (s); 130.29 (d); 129.67 (d); 129.24 (d); 128.61 (d); 126.99 (s); 114.16 (s); 72.51 (t); 63.78 (d); 20.48 (q); 16.26 (q).

EXAMPLE 10

Preparation of the Compound 119 (Table 1)

10.1 g (40.9 mmol) of 3-chloroperoxybenzoic acid (m-CPBA) in 70 ml of dichloromethane is added at 20° C. to a solution of 4.00 g (15.6 mmol) of 6,8-dimethyl-4-phenyl-4H-1-oxa-3-thia-naphthalene [compound 103, Table 1, Example 1] in 100 ml of dichloromethane. The reaction is stirred at room temperature for 10 hours. The organic phase is washed repeatedly with aqueous sodium sulfite, water and brine. The organic phase is dried over magnesium sulfate, filtered and concentrated using a vacuum rotary evaporator to give a crude material which is purified by a flash chromatography (hexane/ethyl acetate: 2:1) to give 2.30 g of the compound 119 as a white solid, m.p. 195-197° C. $^1$H NMR: (400 MHz, CDCl$_3$): δ=7.50-7.40 (m, ArH, 3H); 7.40-7.30 (m, ArH, 2H); 7.01 (s, ArH, 1H); 6.54 (s, ArH, 1H); 5.47 (s, ArCHAr, 1H); 5.01 (d, J=12.0 Hz, OCHHSO$_2$ 1H); 4.93 (d, J=12.0 Hz, OCHHSO$_2$, 1H); 2.31 (s, CH$_3$, 3H); 2.20 (s, CH$_3$, 3H). $^{13}$C NMR: (100 MHz, CDCl$_3$): δ=148.53 (s); 133.13 (s); 132.29 (d); 131.72 (s); 131.00 (d); 129.39 (d); 128.83 (d); 128.83 (d); 128.04 (s); 119.59 (s); 77.17 (t); 67.78 (d); 20.45 (q); 16.24 (q).

EXAMPLE 11

Preparation of the Compound 120 (Table 1)

To a solution of 9.00 g (40.4 mmol) of the compound 101 [Table 1, Example 1] in 100 ml of methanol is added dropwise a solution of 8.70 g (40.4 mmol) of sodium periodate in 50 ml of water. The reaction is stopped after 2 days. Dichloromethane is added and the organic phase is washed with water. The organic phase is dried over magnesium sulfate, filtered and concentrated using a vacuum rotary evaporator to give 10.5 g of a purple liquid. The crude product is purified by flash chromatography (dichloromethane/methanol: 40:1) to give 6.00 g of the compound 120 as white solid, m.p. 127-128° C. $^1$H-NMR: (400 MHz, CDCl$_3$): δ=7.11 (s, ArH, 1H); 6.91 (s, ArH, 1H); 5.16 (d, J=10.8 Hz, OCHHSO, 1H); 4.66 (d, J=10.8 Hz, OCHHSO, 1H); 4.11 (d, J=14 Hz, ArCHHSO, 1H); 3.93 (d, J=14 Hz, ArCHHSO, 1H); 2.32 (s, CH$_3$, 3H); 1.39 (s; tert-butyl; 9H). $^{13}$C NMR: (100 MHz, CDCl$_3$): δ=151.60 (s); 139.70 (s); 133.17 (s); 129.12 (d); 127.92 (d); 118.40 (s); 85.33 (t); 49.63 (t); 34.45 (s); 29.99 (q); 21.01 (q).

EXAMPLE 12

Preparation of the Compound 210 (Table 2)

7.37 g (60.3 mmol) of 2,4-dimethylphenol, 16.9 g (60.3 mmol) of 1H,1H,2H,2H-perfluorohexane-1-thiol, 0.82 g (60.3 mmol) of dimethylamine (33% in ethanol), 3.62 g (120.6 mmol) of paraformaldehyde and 2 ml of N,N-dimethylformamide (DMF) are mixed and heated under reflux for 3 hours under nitrogen atmosphere. Ethyl acetate is added and the organic phase is washed repeatedly with water and brine until pH neutral. The organic phase is dried over sodium sulfate, filtered and concentrated using a vacuum rotary evaporator to give 24.5 g of a yellow liquid. The crude product is purified by flash chromatography (hexane/ethyl acetate: 19:1) to give 23.3 g of the compound 210 as colourless liquid. $^1$H NMR: (400 MHz, CDCl$_3$): δ=6.91 (s, ArH, 1H); 6.75 (s, ArH, 1H); 6.15-5.60 (br s, OH, 1H); 3.80 (s, ArCH$_2$, 2H); 2.75-2.60 (m, CH$_2$CH$_2$CF$_2$, 2H); 2.45-2.15 (m, CH$_2$CH$_2$CF$_2$, 2H); 2.26 (s, CH$_3$, 6H). $^{13}$C NMR: (100 MHz, CDCl$_3$): δ=150.66 (s); 131.38 (d); 129.65 (s); 128.63 (d).

In analogy to Example 12 starting from the corresponding starting materials compounds 211, 205 and 207 (see Table 2) are prepared.

Compound 211: Colourless liquid. $^1$H NMR: (300 MHz, CDCl$_3$): δ=7.08 (s, ArH, 1H); 6.78 (s, ArH, 1H); 6.28 (s, OH, 1H); 3.84 (s, ArCH$_2$S, 2H); 2.70-2.60 (m, CH$_2$CH$_2$CF$_2$, 2H); 2.40-2.10 (m, CH$_2$CH$_2$CF$_2$, 2H); 2.24 (s, CH$_3$, 3H); 1.43 (s, tert-butyl; 9H). $^{13}$C NMR: (100 MHz, CDCl$_3$): δ=151.77 (s); 137.99 (s); 129.29 (s); 128.78 (d); 127.79 (d); 121.76 (s); 34.66 (s); 33.71 (t); 31.59 (t, $^2$J(C, F)=22 Hz); 29.70 (q); 21.49 (t); 20.66 (q).

Compound 205: Pale yellow liquid. $^1$H NMR: (300 MHz, CDCl$_3$): δ=6.93 (s, ArH, 2H); 6.53 (s, OH, 1H); 3.82 (s, ArCH$_2$S, 4H); 2.70-2.60 (m, CH$_2$CH$_2$CF$_2$, 4H); 2.50-2.20 (m, CH$_2$CH$_2$CF$_2$, 4H); 2.26 (s, CH$_3$, 6H). $^{13}$C NMR: (100 MHz, CDCl$_3$): δ=151.00 (s); 130.67 (d); 130.21 (s); 123.75 (s); 31.60 (t, $^2$J(C, F)=22 Hz); 31.55 (t); 21.53 (t); 20.19 (q).

Compound 207: Colourless liquid. $^1$H NMR: (300 MHz, CDCl$_3$): δ=7.06 (s, ArH, 1H); 6.92 (s, ArH, 1H); 6.04 (s, OH, 1H); 3.83 (s, ArCH$_2$S, 2H); 3.66 (s, ArCH$_2$S, 2H); 2.70-2.55 (m, CH$_2$CH$_2$CF$_2$, 4H); 2.45-2.15 (m, CH$_2$CH$_2$CF$_2$, 4H), 2.27 (s, CH$_3$, 3H). $^{13}$C NMR: (100 MHz, CDCl$_3$): δ=152.35 (s); 131.15 (d); 129.21 (d); 128.53 (d); 125.88 (s); 121.83 (s); 35.66 (t); 32.38 (t); 31.61 (t, $^2$J(C, F)=22 Hz); 31.44 (t, $^2$J(C, F)=22 Hz); 21.69 (t); 21.43 (t); 15.65 (q).

EXAMPLE 13

Preparation of the Compound 212 (Table 2)

A mixture of 3.30 g (8.70 mmol) of 2,4-di-tert-butyl-6-(phenylpiperidin-1-yl-methyl)phenol and 4.88 g (17.4 mmol) of 1H,1H,2H,2H-perfluorohexane-1-thiol in 20 ml of toluene is heated under reflux for 2 days under nitrogen atmosphere. Toluene is added and the organic phase is washed repeatedly with water, 1 N HCl and brine until pH neutral. The organic phase is dried over magnesium sulfate, filtered and concentrated using a vacuum rotary evaporator to give 5.90 g of a yellow-orange liquid. The crude product is purified by flash chromatography (hexane/ethyl acetate: 40:1) to give 2.30 g of the compound 212 as yellow liquid. $^1$H NMR: (400 MHz, CDCl$_3$): δ=7.50-7.25 (m, ArH, 5H); 6.90 (s, ArH, 1H); 6.80 (s, ArH, 1H); 5.43 (s, ArCH, 1H); 2.72 (t, J=8.2 Hz, CH$_2$CH$_2$CF$_2$, 2H); 2.35-2.10 (m, CH$_2$CH$_2$CF$_2$, 2H); 1.47 (s, tert-butyl, 9H); 1.25 (s, tert-butyl, 9H). $^{13}$C NMR: (100 MHz, CDCl$_3$): δ=151.48 (s); 142.51 (s); 138.09 (s); 137.55 (s); 128.72 (d); 128.59 (d); 127.85 (d); 124.89 (d); 124.22 (d); 123.36 (s); 52.94 (d); 35.06 (s); 34.27 (s); 31.43 (q); 31.32 (t, $^2$J(C, F)=22.0 Hz); 29.77 (q); 23.09 (t).

In analogy to Example 13 starting from the corresponding starting materials compounds 203 and 204 (see Table 2) are prepared.

Compound 203: Yellow liquid. $^1$H NMR: (300 MHz, CDCl$_3$): δ=7.50-7.20 (m, ArH, 5H); 6.92 (s, ArH, 1H); 6.68 (s, ArH, 1H); 5.42 (s, ArCHAr, 1H); 4.25-4.05 (m, CO$_2$CH$_2$, 2H); 2.95-2.65 (m, SCH$_2$CH$_2$CO$_2$, 4H); 2.27 (s, ArCH$_3$, 3H); 2.19 (s, ArCH$_3$, 3H); 1.70-1.55 (m, CO$_2$CH$_2$CH$_2$, 2H); 1.50-1.30 (m, CO$_2$CH$_2$CH$_2$CH$_2$, 2H); 1.05-0.85 (m, CH$_3$, 3H).

Compound 204: Colourless liquid. $^1$H NMR: (400 MHz, CDCl$_3$): δ=7.55-7.25 (m, ArH, 5H); 7.03 (s, ArH, 1H); 6.76 (d, J=2.4 Hz, ArH, 1H); 5.39 (s, ArCH, 1H); 4.10 (t, J=7.2 Hz, CO$_2$CH$_2$, 2H); 2.75-2.50 (m, SCH$_2$CH$_2$CO$_2$, 4H); 1.70-1.55 (m, CO$_2$CH$_2$CH$_2$, 2H); 1.44 (s, tert-butyl, 9H); 1.44-1.30 (m, CO$_2$CH$_2$CH$_2$CH$_2$, 2H); 1.19 (s, tert-butyl, 9H); 0.93 (t, J=7.2 Hz, CH$_3$, 3H). $^{13}$C NMR: (100 MHz, CDCl$_3$): δ=171.82 (s); 151.60 (s); 142.05 (s); 138.68 (s); 137.34 (s); 128.90 (d); 128.62 (d); 127.65 (d); 124.77 (d); 124.21 (s); 123.79 (d); 64.78 (t); 52.10 (d); 35.13 (s); 34.29 (s); 34.12 (s); 31.54 (q); 30.64 (t); 29.87 (q); 27.31 (t); 19.16 (t); 13.75 (q).

EXAMPLE 14

Preparation of the Compound 202 (Table 2)

2,4-dimethylphenol (16.5 g, 135 mmol), butyl 3-mercaptopropionate (21.9 g, 135 mmol), dimethylamine (33% in ethanol) (0.61 g, 0.14 mmol), paraformaldehyde (8.11 g, 270 mmol) and N,N-dimethylformamide (DMF) (5.0 ml) were mixed and heated under reflux for 2 hours under nitrogen atmosphere. Ethyl acetate was added and the organic phase was washed repeatedly with water and brine until pH neutral. The organic phase was dried over magnesium sulfate, filtered and concentrated using a vacuum rotary evaporator to give 61.3 g of a pale yellow liquid. The crude product is purified by flash chromatography (hexane/ethyl acetate: 9:1) to give 39.2 (98%) of compound 202 as a colourless liquid. $^1$H NMR (300 MHz, CDCl$_3$): δ=6.91 (s, ArH, 1H), 6.77 (s, ArH, 1H); 6.27 (s, OH, 1H); 4.12 (t, J=6.6 Hz, CO$_2$CH$_2$, 2H); 3.80 (s, ArCH$_2$S, 2H); 2.78-2.55 (m, SCH$_2$CH$_2$CO$_2$, 4H); 2.24 (s, ArCH$_3$, 6H); 1.70-1.55 (m, CO$_2$CH$_2$CH$_2$, 2H); 1.50-1.40 (m, CO$_2$CH$_2$CH$_2$CH$_2$, 2H); 0.96 (t, J=7.2 Hz, CH$_3$, 3H). $^{13}$C NMR (100 MHz, CDCl$_3$): 171.95 (s); 151.11 (s); 131.23 (d); 129.24 (s); 128.57 (d); 125.64 (s); 121.52 (s); 64.74 (t); 34.38 (t); 32.89 (t); 30.61 (t); 25.85 (t); 20.39 (q); 19.12 (t); 15.83 (q); 13.68 (q).

In analogy to Example 14 starting from the corresponding starting materials compounds 201 and 206 (see Table 2) are prepared.

Compound 201: Yellow liquid. $^1$H NMR: (300 MHz, CDCl$_3$): δ=7.06 (s, ArH, 1H); 6.79 (s, ArH, 1H); 6.59 (br s, OH, 1H); 4.13 (t, J=6.6 Hz, CO$_2$CH$_2$, 2H); 3.82 (s, ArCH2S, 2H); 2.75-2.50 (m, SCH$_2$CH$_2$CO$_2$, 4H); 2.27 (s, ArCH$_3$, 3H); 1.70-1.55 (m, CO$_2$CH$_2$CH$_2$, 2H); 1.43 (s, tert-butyl, 9H); 1.45-1.30 (m, CO$_2$CH$_2$CH$_2$CH$_2$, 2H); 0.96 (t, J=7.2 Hz, CH$_3$, 3H). $^{13}$C NMR: (100 MHz, CDCl$_3$): δ=171.78 (s); 152.12 (s); 137.88 (s); 128.86 (s); 128.86 (d); 127.53 (d); 122.12 (s); 64.71 (t); 34.70 (s); 34.40 (t); 33.75 (t); 30.62 (t); 29.75 (q); 25.82 (t); 20.76 (q); 19.11 (t); 13.68 (q).

Compound 206: Colourless liquid. $^1$H NMR: (400 MHz, CDCl$_3$): δ=6.91 (s, ArH, 1H); 6.80 (s, OH, 1H); 4.10 (t, J=6.8 Hz, CO$_2$CH$_2$, 4H); 3.78 (s, ArCH$_2$S, 4H); 2.80-2.50 (m, SCH$_2$CH$_2$CO$_2$, 8H); 2.24 (s, ArCH$_3$, 3H); 1.70-1.55 (m, CO$_2$CH$_2$CH$_2$, 4H); 1.50-1.30 (m, CO$_2$CH$_2$CH$_2$CH$_2$, 4H); 0.93 (t, J=7.2 Hz, CH$_3$, 6H). $^{13}$C NMR: (100 MHz, CDCl$_3$): δ=172.04 (s); 151.20 (s); 130.45 (d); 129.61 (s); 124.12 (s); 64.66 (t); 34.51 (t); 31.70 (t); 30.62 (t); 26.12 (t); 20.45 (q); 19.13 (t); 13.72 (q).

TABLE 1

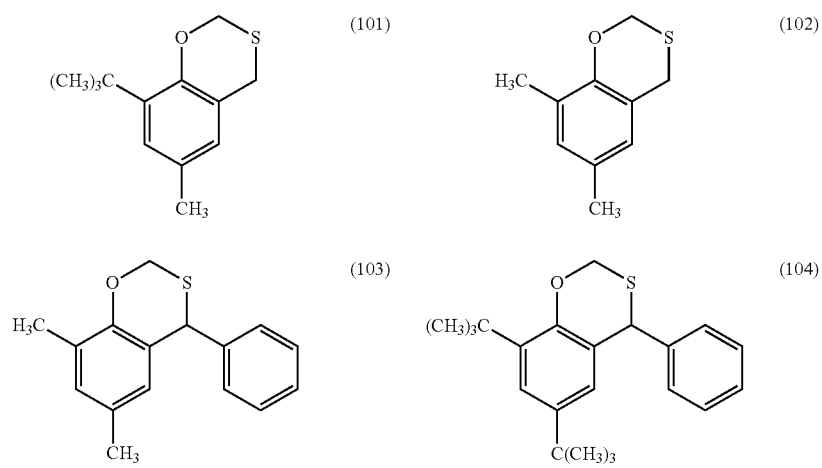

TABLE 1-continued
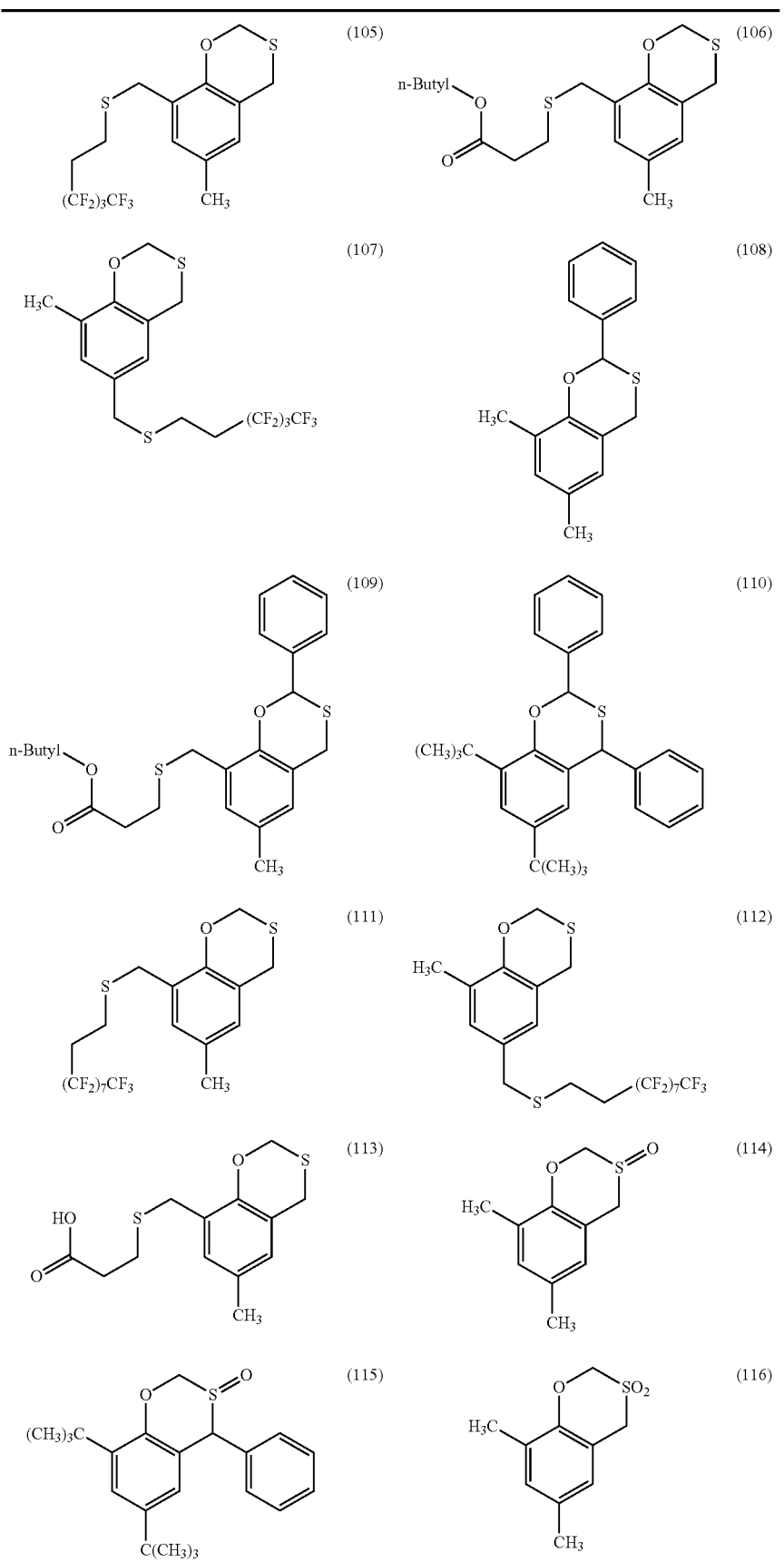

TABLE 1-continued
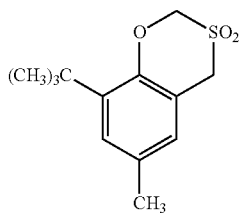 [SMILES: Cc1cc2c(c(C(C)(C)C)c1)OCS(=O)(=O)C2] (117)
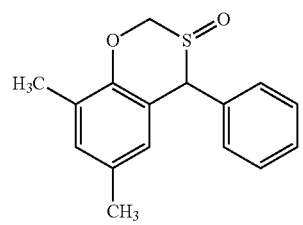 [SMILES: Cc1cc(C)c2c(c1)C(c1ccccc1)S(=O)CO2] (118)
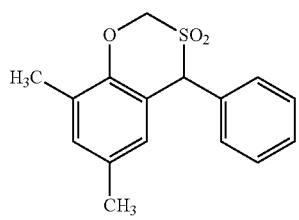 [SMILES: Cc1cc(C)c2c(c1)C(c1ccccc1)S(=O)(=O)CO2] (119)
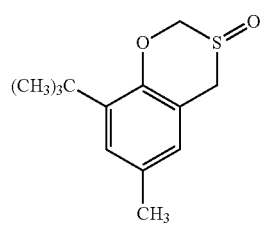 [SMILES: Cc1cc2c(c(C(C)(C)C)c1)OCS(=O)C2] (120)
TABLE 2
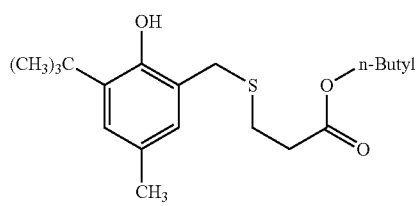 (201)
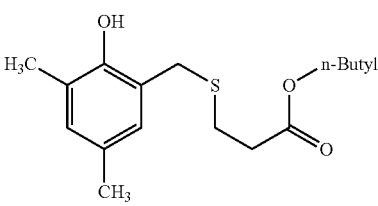 (202)
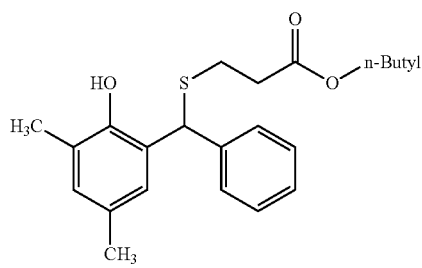 (203)
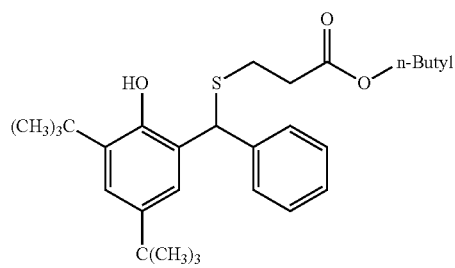 (204)
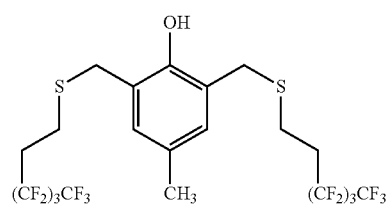 (205)
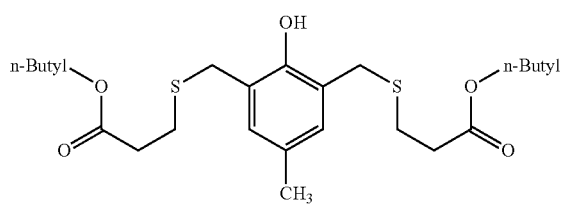 (206)
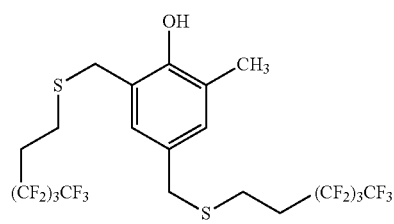 (207)
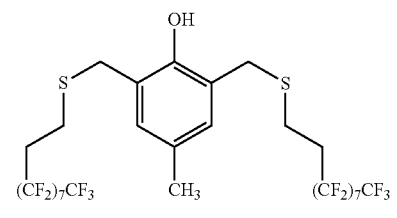 (208)

TABLE 2-continued

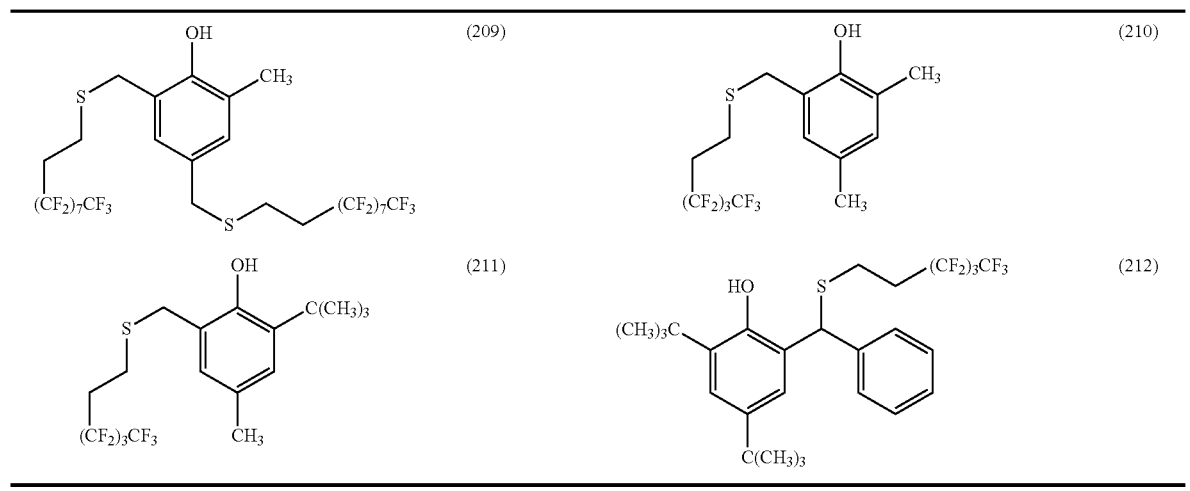

EXAMPLE 15

Stabilization of Multiple-Extruded Polypropylene 1.3 kg of polypropylene powder (Moplen HF 500 N) is blended with 0.05% of Irganox®1010 (pentaerythritol tetrakis[3-(3,5-di-tert-butyl-4-hydroxyphenyl)propionate]), 0.05% of calcium stearate, 0.02% of Irgafos®168 [tris(2,4-ditert-butylphenyl)phosphite] and 0.02% of a compound according to the invention. This blend is then extruded in an extruder having a cylinder diameter of 20 mm and a length of 400 mm at 100 rpm, the 3 heating zones being adjusted to the following temperatures: 260, 270, 280° C. The extrudate is cooled by drawing it through a water bath and is then granulated. This granulate is repeatedly extruded. After 3 extrusions, the melt index is measured (at 230° C./2.16 kg). A substantial decrease in the melt index denotes good stabilization, for example limited polymeric chain degradation. The results are summarized in Table 3.

TABLE 3

| Compound of Table 1 | Melt index after 3 extrusions |
| --- | --- |
| — | 69.0 |
| 103 | 17.7 |
| 118 | 14.8 |
| 119 | 20.3 |

EXAMPLE 16

Water and Oil Repellency in Polypropylene

In order to determine the repellency properties of the compounds according to the invention, they are tested according to the following procedure. The sample preparation is a combination of polypropylene nonwovens and the additive and a thermal treatment (e.g. 130° C. for 10 minutes), which enables the migration of the additive to the surface and a proper surface rearrangement of the chemical groups. This extra heat cycle is needed to melt the compounds of the formula I in order to obtain a homogeneous redistribution over the surface of the substrate. An industrial sample of polypropylene nonwoven, fabric weight: 40 g/m², is dipped into a 1% isopropanol solution of the test compound, simultaneously applying ultrasonic energy for one minute. After that, the sample is dried overnight at room temperature and then two hours at 90° C. in an oven. A part of the sample is afterwards annealed for 10 minutes at 130° C.

The treated nonwoven samples are evaluated in the water repellency test similar to INDA test method 80.8 (99). The wetting behavior of the nonwovens is tested with a series of water/isopropanol mixtures. The observation of the wetting behavior is rated from 0 (water wetting, no repellency) to 10 (optimum water repellency). The results are summarized in Table 4.

The treated nonwoven samples are evaluated in the oil repellency test similar to AATCC test method 118-1997/ISO 14419. This test follows the same concepts of the already described for water repellency test method, but using, as test solvents, a series of hydrocarbons. The observation of the wetting behavior is rated from 0 (no repellency) to 8 (optimum repellency).

TABLE 4

| Example | Compound | Water repellency After drying | Water repellency After annealing |
| --- | --- | --- | --- |
| 16a | 112 | 7 | 4 |

EXAMPLE 17

Scorch Resistance of Polyether/Polyurethane Soft Foams 0.71 g (0.45%, based on the polyol) of a stabilizer composition based on the compound 101 according to the invention is dissolved in 157.1 g of Lupranol 2084® [trifunctional polyether polyol containing predominantly secondary hydroxyl groups; hydroxyl number 48 mg KOH/g, water content less than 0.1%, acid number less than 0.06 mg KOH/g] supplied by Elastogran BASF. Then 9.84 g of a solution consisting of 1.88 g Tegostab® BF 2370 [polysiloxane polyoxyalkylene block copolymer] supplied by Evonik Industries, Germany, 0.24 g Tegoamin® 33 [33% solution of triethylamine in dipropylene glycol] supplied by Evonik Industries, Germany and 7.70 g of deionized water are added. The reaction mixture is stirred vigorously for 10 seconds at 2600 rpm. 0.31 g Kosmos® 29 [stannous octanoate] supplied by Evonik Industries, Germany is then added and the reaction mixture is again stirred vigorously for 18 seconds at 2600 rpm. 92.19 g of Lupranat® T80 [mixture of 2,4- and 2,6-toluene diisocyanate] supplied by Elastogran BASF is then added with continuous stirring for 5 to 7 seconds at 2600 rpm. The mixture is then poured into a 20×20×20 cm cake-box and the exothermic temperature is measured during foaming to a foam block. The foam blocks are cooled and stored at room temperature for 24 hours. The next day the foams are cut into thin tubes (2 cm thick, 1.5 cm in diameter).

Dynamic heat ageing of foam samples is used as a measure of scorch resistance (Dynamic Alu Block Test). The foam samples are typically heated in an oven or an aluminum block and scorch resistance is assessed by measuring the color change. In the "dynamic" heat ageing test the temperature is increased at a constant rate and the color change determined as a function of the temperature (30 minutes at temperatures between 170 and 230° C.). The foam color quality is reported in terms of Yellowness Index (YI) determined on the foam samples in accordance with the ASTM 1926-70 Yellowness Test. Low YI values denote little discoloration, high YI values severe discoloration of the samples. The whiter the foam the better is the foam stabilized. The results are summarized in Table 5.

TABLE 5

| | YI after dynamic heat ageing | | | | | |
|---|---|---|---|---|---|---|
| Compound of Table 1 | 170° C. | 180° C. | 190° C. | 200° C. | 210° C. | 220° C. |
| — | 1.6 | 9.7 | 19.4 | 31.1 | 52.6 | 64 |
| composition based on the compound 101 | −1.3 | 0.2 | 4.4 | 17.2 | 34.5 | 51.1 |

What is claimed is:

1. A composition, comprising:
    a) an organic material susceptible to oxidative, thermal or light-induced degradation, wherein the organic material comprises an organic polymer, a lubricant, or a fuel; and
    b) at least one compound of formula (I):

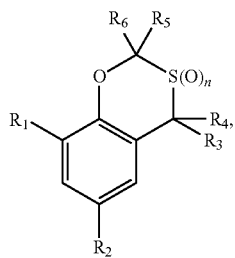

wherein:
    $R_1$ and $R_2$ are each independently hydrogen, $C_1$-$C_{25}$alkyl, $C_2$-$C_{25}$alkenyl, phenyl optionally substituted by $C_1$-$C_4$ alkyl, $C_7$-$C_9$-phenylalkyl optionally substituted by $C_1$-$C_4$ alkyl, —CH($R_7$)—S(O)$_n$—$R_8$, or —CH($R_{7a}$)—S(O)$_n$—CH$_2$—CH($R_{7b}$)—$R_9$;
    $R_3$ and $R_4$ are each independently hydrogen, $C_1$-$C_{25}$alkyl, or phenyl optionally substituted by $C_1$-$C_4$ alkyl;
    $R_5$ and $R_6$ are each independently hydrogen, $C_1$-$C_{25}$alkyl, $C_2$-$C_{25}$alkyl interrupted by oxygen phenyl optionally substituted by $C_1$-$C_4$ alkyl, halogen, —CN, —NO$_2$,

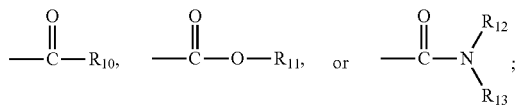

$R_7$, $R_{7a}$, and $R_{7b}$ are each independently hydrogen, $C_1$-$C_{12}$alkyl,

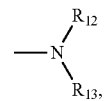

phenyl optionally substituted by halogen or $C_1$-$C_4$ alkyl;
    $R_8$ is a monovalent perfluorinated alkyl or alkenyl, linear or branched organic radical having four to twenty fully fluorinated carbon atoms;
    $R_9$ is —CN, —S(O)$_n$—$R_{10}$,

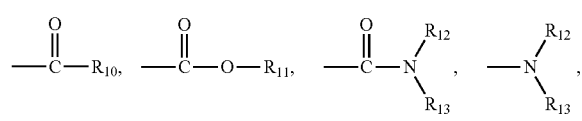

or —NO$_2$;
    $R_{10}$ is hydrogen, $C_1$-$C_{25}$alkyl, $C_7$-$C_9$-phenylalkyl, phenyl optionally substituted by $C_1$-$C_4$ alkyl, $C_5$-$C_8$cycloalkyl optionally substituted by $C_1$-$C_4$ alkyl;
    $R_{11}$ is hydrogen, alkali metal, $C_1$-$C_{25}$alkyl, $C_7$-$C_9$-phenylalkyl, phenyl optionally substituted by $C_1$-$C_4$ alkyl, $C_5$-$C_8$cycloalkyl optionally substituted by $C_1$-$C_4$ alkyl, or $C_3$-$C_{25}$alkyl which is interrupted by oxygen or sulfur;
    $R_{12}$ and $R_{13}$ are each independently hydrogen, $C_1$-$C_{25}$alkyl, $C_1$-$C_4$alkanoyl, $C_7$-$C_9$-phenylalkyl, phenyl optionally substituted by $C_1$-$C_4$ alkyl, or $R_{12}$ and $R_{13}$, together with the nitrogen atom to which they are attached, form a 5-, 6-1 or 7-membered heterocyclic ring which is optionally substituted by $C_1$-$C_4$alkyl or is interrupted by oxygen, sulfur or

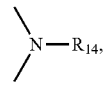

$R_{14}$ is hydrogen, $C_1$-$C_8$alkyl, or benzyl; and
n is 0, 1, or 2.

2. The composition of claim 1, wherein, in formula (I):
    $R_1$ and $R_2$ are each independently hydrogen, $C_1$-$C_{18}$alkyl, $C_{18}$alkenyl, phenyl optionally substituted by $C_1$-$C_4$ alkyl, $C_7$-$C_9$-phenylalkyl optionally substituted by $C_1$-$C_4$ alkyl, —CH($R_7$)—S(O)$_8$—$R_8$, or —CH($R_{7a}$)—S (O)$_n$—CH$_2$—CH($R_{7b}$)—$R_9$;
    $R_3$ and $R_4$ are each independently hydrogen, $C_1$-$C_{18}$alkyl, or phenyl optionally substituted by $C_1$-$C_4$ alkyl;
    $R_5$ and $R_6$ are each independently hydrogen, $C_1$-$C_{18}$alkyl, $C_{18}$alkyl interrupted by oxygen, phenyl optionally substituted by $C_1$-$C_4$ alkylan halogen, —CN,

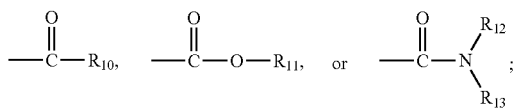

R$_7$, R$_{7a}$, and R$_{7b}$ are each independently hydrogen, C$_1$-C$_{12}$alkyl, or phenyl;

R$_8$ is a monovalent perfluorinated alkyl or alkenyl, linear or branched organic radical having four to twenty fully fluorinated carbon atoms;

R$_9$ is —CN, —S(O)$_n$—R$_{10}$,

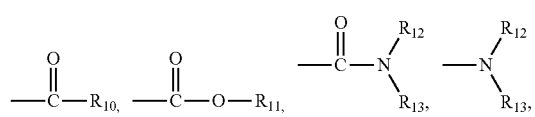

or —NO$_2$;

R$_{10}$ is hydrogen, C$_1$-C$_{18}$alkyl, C$_7$-C$_9$-phenylalkyl, phenyl optionally substituted by C$_1$-C$_4$ alkyl; C$_5$-C$_8$cycloalkyl optionally substituted by C$_1$-C$_4$ alkyl;

R$_{11}$ is hydrogen, C$_1$-C$_{18}$alkyl, C$_7$-C$_9$-phenylalkyl, phenyl optionally substituted by C$_1$-C$_4$ alkyl, C$_5$-C$_8$cycloalkyl optionally substituted by C$_1$-C$_4$ alkyl, or C$_3$-C$_{18}$alkyl which is interrupted by oxygen or sulfur;

R$_{12}$ and R$_{13}$ are each independently hydrogen, C$_1$-C$_{18}$alkyl, C$_7$-C$_9$-phenylalkyl, phenyl optionally substituted by C$_1$-C$_4$ alkyl, or R$_{12}$ and R$_{13}$, together with the nitrogen atom to which they are attached, form a 5-, 6- or 7-membered heterocyclic ring which is optionally substituted by C$_1$-C$_4$alkyl or is interrupted by oxygen, sulfur or

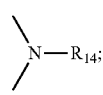

R$_{14}$ is hydrogen, C$_1$-C$_8$alkyl, or benzyl; and n is 0, 1 or 2.

3. The composition according to of claim 1, wherein, in formula (I):

R$_1$ and R$_2$ are each independently hydrogen, C$_1$-C$_{12}$alkyl, phenyl, benzyl, —CH(R$_7$)—S(O)$_n$—R$_8$, or —CH(R$_{7a}$)—S(O)$_n$—CH$_2$—CH(R$_{7b}$)—R$_9$;

R$_3$ and R$_4$ are each independently hydrogen, C$_1$-C$_{12}$alkyl, or phenyl;

R$_5$ and R$_6$ are each independently hydrogen, C$_1$-C$_{12}$alkyl, phenyl, halogen, —CN,

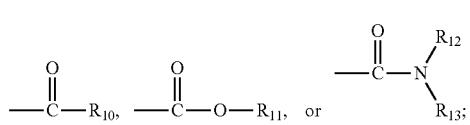

R$_7$, R$_{7a}$, and R$_{7b}$ are each independently hydrogen or C$_1$-C$_{12}$alkyl;

R$_8$ is —(CF$_2$)$_m$CF$_3$ or —CH$_2$—CH$_2$—(CF$_2$)$_m$CF$_3$,

R$_9$ is —CN,

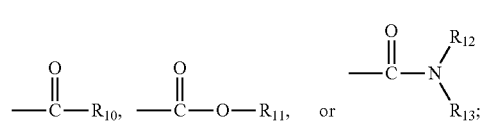

R$_{10}$ is C$_1$-C$_{12}$alkyl, C$_7$-C$_9$-phenylalkyl, phenyl, or C$_5$-C$_8$cycloalkyl;

R$_{11}$ is hydrogen, C$_1$-C$_{12}$alkyl, benzyl, phenyl, C$_5$-C$_8$cycloalkyl, or C$_3$-C$_{18}$alkyl;

R$_{12}$ and R$_{13}$ are each independently hydrogen, C$_1$-C$_{12}$alkyl, benzyl, phenyl, or R$_{12}$ and R$_{13}$, together with the nitrogen atom to which they are attached, form a 6-membered heterocyclic ring;

m is 3 to 12; and n is 0, 1 or 2.

4. The composition of claim 1, wherein, in formula (I):

R$_1$ is C$_1$-C$_4$alkyl, —CH(R$_7$)—S(O)$_n$—R$_8$, or —CH(R$_{7a}$)—S(O)$_n$—CH$_2$—CH(R$_{7b}$)—R$_9$;

R$_2$ is C$_1$-C$_4$alkyl, —CH(R$_7$)—S(O)$_n$—R$_8$ or —CH(R$_{7a}$)—S(O)$_n$—CH$_2$—CH(R$_{7b}$)—R$_9$;

R$_3$ is hydrogen;

R$_4$ is hydrogen or phenyl;

R$_5$ is hydrogen;

R$_6$ is hydrogen or phenyl;

R$_7$, R$_{7a}$, and R$_{7b}$ are hydrogen,

R$_8$ is —CH$_2$—CH$_2$—(CF$_2$)$_3$CF$_3$ or —CH$_2$—CH$_2$—(CF$_2$)$_7$CF$_3$;

R$_9$ is

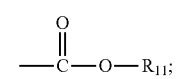

R$_{11}$ is hydrogen or C$_1$-C$_8$alkyl; and n is 0, 1 or 2.

5. The composition of claim 1, wherein the organic material a) comprises a natural, semisynthetic, or synthetic polymer.

6. The composition of claim 1, wherein the organic material a) comprises thermoplastic polymer.

7. The composition of claim 1, wherein the organic material a) comprises a polyolefin.

8. The composition of claim 1, comprising from 0.0005 to 10% of the compound of formula (I), based on the weight of a).

9. The composition of claim 1, further comprising:

an additive.

10. The composition of claim 9, wherein the additive is at least one selected from the group consisting of a phenolic antioxidant, a light-stabilizer, and a processing stabilizer.

11. A process for stabilizing an organic material against oxidative, thermal or light-induced degradation and/or for reducing the surface energy of organic materials, the process comprising:

incorporating therein or applying thereto at least a compound of formula (I):

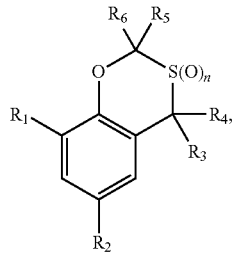

wherein:
R$_1$ and R$_2$ are each independently hydrogen, C$_1$-C$_{25}$alkyl, C$_2$-C$_{25}$alkenyl, phenyl optionally substituted by C$_1$-C$_4$ alkyl, C$_7$-C$_9$-phenylalkyl optionally substituted by C$_1$-C$_4$ alkyl, —CH(R$_7$)—S(O)$_n$—R$_8$, or —CH(R$_{7a}$)—S(O)$_n$—CH$_2$—CH(R$_{7a}$)—R$_9$;
R$_3$ and R$_4$ are each independently hydrogen, C$_1$-C$_{25}$alkyl, or phenyl optionally substituted by C$_1$-C$_4$ alkyl;
R$_5$ and R$_6$ are each independently hydrogen, C$_1$-C$_{25}$alkyl, C$_{25}$alkyl interrupted by oxygen phenyl optionally substituted by C$_1$-C$_4$ alkyl, halogen, —CN, —NO$_2$,

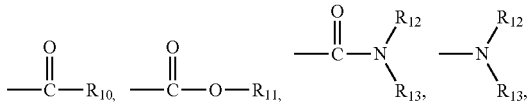

R$_7$, R$_{7a}$ and R$_{7b}$ are each independently hydrogen, C$_1$-C$_{12}$alkyl,

phenyl optionally substituted by halogen or C$_1$-C$_4$ alkyl;

R$_8$ is a monovalent perfluorinated alkyl or alkenyl, linear or branched organic radical having four to twenty fully fluorinated carbon atoms;
R$_9$ is —CN, —S(O)$_n$—R$_{10}$,

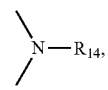

or —NO$_2$;
R$_{10}$ is hydrogen, C$_1$-C$_{25}$alkyl, C$_7$-C$_9$-phenylalkyl, phenyl optionally substituted by C$_1$-C$_4$ alkyl, C$_5$-C$_8$cycloalkyl optionally substituted by C$_1$-C$_4$ alkyl;
R$_{11}$ is hydrogen, alkali metal, C$_1$-C$_{25}$alkyl, C$_7$-C$_9$-phenylalkyl, phenyl optionally substituted by C$_1$-C$_4$ alkyl, C$_5$-C$_8$cycloalkyl optionally substituted by C$_1$-C$_4$ alkyl, or C$_3$-C$_{25}$alkyl which is interrupted by oxygen or sulfur;
R$_{12}$ and R$_{13}$ are each independently hydrogen, C$_1$-C$_{25}$alkyl, C$_1$-C$_4$alkanoyl, C$_7$-C$_9$phenylalkyl, phenyl optionally substituted by C$_1$-C$_4$ alkyl, or R$_{12}$ and R$_{13}$, together with the nitrogen atom to which they are attached, form a 5-, 6- or 7-membered heterocyclic ring which is optionally substituted by C$_1$-C$_4$alkyl or is interrupted by oxygen, sulfur, or $$\diagdown N-R_{14},$$

R$_{14}$ is hydrogen, C$_1$-C$_8$alkyl, or benzyl and
n is 0, 1 or 2.

12. The composition of claim 1, wherein the organic material a) comprises the organic polymer.

13. The composition of claim 1, wherein the organic material a) comprises a polyolefin or a polyurethane.

* * * * *